US012715840B2

(12) United States Patent
Nagahama et al.

(10) Patent No.: US 12,715,840 B2
(45) Date of Patent: Aug. 25, 2026

(54) METHOD FOR MANUFACTURING AROMATIC NITRILE COMPOUND

(71) Applicant: UBE Corporation, Yamaguchi (JP)

(72) Inventors: Masaki Nagahama, Chiyoda-ku (JP); Hideki Oomiya, Zaventem (BE); Daiki Okado, Chiyoda-ku (JP); Hirotsugu Taniike, Chiyoda-ku (JP)

(73) Assignee: UBE Corporation, Yamaguchi (JP)

(*) Notice: Subject to any disclaimer, the term of this patent is extended or adjusted under 35 U.S.C. 154(b) by 73 days.

(21) Appl. No.: 18/738,245

(22) Filed: Jun. 10, 2024

(65) Prior Publication Data

US 2024/0351978 A1 Oct. 24, 2024

Related U.S. Application Data

(62) Division of application No. 17/050,255, filed as application No. PCT/JP2019/018065 on Apr. 26, 2019, now Pat. No. 12,054,448.

(60) Provisional application No. 62/780,445, filed on Dec. 17, 2018, provisional application No. 62/663,014, filed on Apr. 26, 2018.

(51) Int. Cl.

| | |
|---|---|
| ***C07C 51/06*** | (2006.01) |
| ***C07C 253/20*** | (2006.01) |
| *C07C 57/38* | (2006.01) |
| *C07C 255/33* | (2006.01) |

(52) U.S. Cl.
CPC ............ *C07C 253/20* (2013.01); *C07C 51/06* (2013.01); *C07C 57/38* (2013.01); *C07C 255/33* (2013.01); *C07C 2602/10* (2017.05)

(58) Field of Classification Search
CPC .............................. C07C 51/06; C07C 253/20
See application file for complete search history.

(56) References Cited

U.S. PATENT DOCUMENTS

| | | | |
|---|---|---|---|
| 11,643,386 | B2 | 5/2023 | Nagahama et al. |
| 2005/0182269 | A1 | 8/2005 | Ashworth et al. |
| 2022/0281806 | A1 | 9/2022 | Nagahama. et al. |
| 2023/0227400 | A1 | 7/2023 | Nagahama et al. |

FOREIGN PATENT DOCUMENTS

| | | | |
|---|---|---|---|
| JP | 61-268650 | A | 11/1986 |
| JP | 2001-39904 | A | 2/2001 |
| JP | 2005-529973 | A | 10/2005 |
| WO | WO 2007/016155 | A2 | 2/2007 |
| WO | WO 2014/001939 | A1 | 1/2014 |
| WO | WO 2015/089111 | A1 | 6/2015 |
| WO | WO 2015/102826 | A1 | 7/2015 |

OTHER PUBLICATIONS

Chinese Decision of Reexamination issued Jan. 22, 2025 in Chinese Patent Application No. 201980028082.1 (with English translation), 37 pages.

Extended European Search Report issued Apr. 30, 2025 in European Patent Application No. 24219154.2, 8 pages.

Price, C. et al., "The Preparation of Several Chlorinated 1-Vinylnaphthalenes," The Journal of Organic Chemistry, 1949, vol. 14, pp. 111-117.

Alam, M.M. et al., "A Facile Synthesis of Phenylacetic Acids via Willgerodt-Kindler Reaction Under PTC Condition," Synthetic Communications, 2003, vol. 33, No. 1, pp. 59-63.

Hulkenberg, A. et al., "An Efficient One-Pot Synthesis of Nitriles From Acid Chlorides," Tetrahedron Letters, 1982, vol. 23, No. 14, pp. 1505-1508.

International Search Report issued on Aug. 6, 2019 in PCT/JP2019/018065 filed on Apr. 26, 2019, 2 pages.

Huddar, S. N. et al., "Oxidative rearrangement of alkyl aryl/heteroaryl ketones by 1,2-aryl-heteroaryl shift using iodic acid", ARKIVOC 2011 (V), 2010, pp. 67-75, DOI: https://doi.org/10.3998/ark.5550190.0012.508.

(Continued)

*Primary Examiner* — Shawquia Jackson

(74) *Attorney, Agent, or Firm* — Oblon, McClelland, Maier & Neustadt, L.L.P.

(57) ABSTRACT

The present invention provides a method for industrially producing a highly pure aromatic nitrile compound and a highly pure aromatic carboxylic acid compound safely and highly efficiently at low costs. Compound (2) is subjected to Willgerodt reaction in the presence of an additive as necessary, and the obtained amide compound (3) is hydrolyzed and neutralized to give carboxylic acid compound (4). Carboxylic acid compound (4) is reacted with a halogenating agent in the presence of a catalyst as necessary in an organic solvent, and further reacted with an amidating agent, and the obtained amide compound (5) or (6) is reacted with a dehydrating agent to give nitrile compound (1). Alternatively, carboxylic acid compound (4) is reacted with a halogenating agent and a compound represented by the formula $R^6SO_2R^7$ in the presence of a catalyst as necessary in an organic solvent to give nitrile compound (1). Np is a naphthyl group optionally having substituent(s), $R^5$ is an alkylene group having 1-3 carbon atoms, and other symbols are as described in the DESCRIPTION.

(2) (3)

(4)

(4) (5) 又は or (6) (1)

(4) (1)

21 Claims, 5 Drawing Sheets

(56) References Cited

OTHER PUBLICATIONS

Otomatsu, T. et al., "Bioconversion of aromatic compounds by *Escherichia coli* that expresses cytochrome P450 CYP153A13a gene isolated from an alkane-assimilating marine bacterium Alcanivorax borkumensis", Journal of Molecular Catalysis B: Enzymatic 66, 2010, pp. 234-240.
Ashworth, I. W. et al., "A New Route for Manufacture of 3-Cyano-1-naphthalenecarboxylic Acid", Organic Process Research & Development, 2003, 7, pp. 74-81.
Gawande, S. S. et al., "Uncatalyzed synthesis of thiomorpholide using polyethylene glycol as green reaction media", Green Chemistry Letters and Reviews, 2010, 3:4, pp. 315-318, https://doi.org/10.1080/17518253.2010.486772.
Priebbenow, D. et al., "Recent advances in the Willgerodt-Kindler reaction", Chem Soc Rev, 2013, 42, pp. 7870-7880, https://doi.org/10.1039/c3cs60154d.
Gbaguidi, F.A. et al., "General Acid-Base Catalysis in the Willgerodt-Kindler Reaction", J. Soc. Ouest-Afr. Chim. 2010, 029, pp. 89-94.
Written Opinion issued on Aug. 6, 2019 in PCT/JP2019/018065 filed on Apr. 26, 2019, 10 pages.
Extended European Search Report issued May 14, 2021 in European Patent Application No. 19793649.5, 7 pages.
Melvin S. Newman, "New Syntheses of Picene," Journal of Organic Chemistry, vol. 9, No. 6, XP055798169, 1944, pp. 518-528.
Vincent J. Huber, et al., "Preparation of Nitriles from Carboxylic Acids: A New, Synthetically Useful Example of the Smiles Rearrangement," Tetrahedron, vol. 54, XP004127405, 1998, pp. 9281-9288.
Examination Report issued Mar. 5, 2021 in Indian Patent Application No. 202017046832, 6 pages.
Indian Office Action issued Jan. 6, 2022 in Indian Patent Application No. 202017046832 , 2 pages.
Canadian Office Action issued Sep. 20, 2022 in Canadian Patent Application No. 3,098,437, 5 pages.
Combined Chinese Office Action and Search Report issued Oct. 10, 2022 in Patent Application No. 201980028082.1 (with English language translation), 26 pages.
Notice of Grounds for Rejection issued May 8, 2023 in Korean Patent Application No. 10-2020-7033680 (with English language translation), 25 pages.
European Office Action issued May 22, 2023 in European Patent Application No. 19793649.5, 5 pages.
Notice of Reasons for Refusal issued May 23, 2023 in Japanese Patent Application No. 2020-515623 (with English language translation), 7 pages.
Chinese Office Action issued Aug. 1, 2023 in Chinese Patent Application No. 201980028082.1 (with English Translation), 18 pages.
Combined Chinese Office Action and Search Report issued Jan. 5, 2024 in Chinese Application 201980028082.1. (with English translation), 18 pages.
Es, etal. (Journal of the Chemical Society (1964), (Dec.), 5493-4 (abstract), Accession No. 1965:36672, retrieved from STN.
Chinese Office Action issued Sep. 12, 2024 in Chinese Patent Application No. 201980028082.1 (with English translation), 28 pages.
Office Action dated Mar. 19, 2026 issued in the corresponding European patent application No. 24219154.2.
Website, "The Willgerodt Reaction" (Mar. 25, 2016).
Website, N,N-Dimethylformamide: A Multipurpose Building Block (Feb. 15, 2013).
Office Action dated May 26, 2026 issued in the corresponding Korean patent application No. 10-2024-7025451 (with English translation).

The carboxylic acid compound crude crystal

The carboxylic acid compound purified crystal

The carboxylic acid compound ($^{1}$H-NMR)

The amide compound crystal (UV280nm)

The 2-naphthylacetonitrile ($^1$H-NMR)

METHOD FOR MANUFACTURING AROMATIC NITRILE COMPOUND

CROSS-REFERENCE TO RELATED APPLICATIONS

The present application is a Divisional Application of U.S. application Ser. No. 17/050,255, filed Oct. 23, 2020. U.S. application Ser. No. 17/050,255 is a 35 U.S.C. § 371 National Stage Application of International Patent Application PCT/JP2019/018065, filed Apr. 26, 2019, which is based on and claims the benefit of priority to U.S. Application No. 62/663,014, filed Apr. 26, 2018 and U.S. Application No. 62/780,445, filed Dec. 17, 2018. The entire contents of all of the above applications are incorporated herein by reference.

TECHNICAL FIELD

The present invention relates to a method for producing an aromatic nitrile compound, preferably 2-naphthylacetonitrile, useful as a starting material for synthesis, or an intermediate for synthesis of various pharmaceutical products, agricultural chemicals, and chemical products.

Furthermore, the present invention relates to a method for producing an aromatic carboxylic acid compound, preferably 2-naphthylacetic acid (2-naphthaleneacetic acid), useful as a starting material for synthesis, or an intermediate for synthesis of the aromatic nitrile compound of the present invention and also useful as a starting material for synthesis, or an intermediate for synthesis of various pharmaceutical products, agricultural chemicals, and chemical products.

BACKGROUND ART

2-Naphthylacetonitrile is useful as a starting material for synthesis, or an intermediate for synthesis of various pharmaceutical products, agricultural chemicals, and chemical products. In addition, an aromatic nitrile compound having a chemical structure similar to that of 2-naphthylacetonitrile is expected to be usable as a starting material for synthesis, or an intermediate for synthesis of various pharmaceutical products, agricultural chemicals, and chemical products.

For example, 2-naphthylacetonitrile is useful as a starting material for synthesis, or an intermediate for synthesis of pharmaceutical products such as pharmaceutical products used for the prophylaxis, treatment and the like of depression (e.g., major depressive disorder, bipolar disease), fibromyalgia, pain (e.g., neuropathic pain), sleep disorder, attention deficit disorder (ADD), attention deficit hyperactivity disorder (ADHD), restless legs syndrome, schizophrenia, anxiety, obsessive-compulsive disorder, post-traumatic stress disorder, seasonal affective disorder (SAD), premenstrual dystonia, CNS diseases such as neurodegenerative disease (e.g., Parkinson's disease, Alzheimer's disease) and the like, diseases relating to urinary incontinence and irritable bowel syndrome (IBS), diabetes and the like, erythropoietin (EPO) inducer, calcium antagonist, histamine receptor antagonist, tachykinin receptor antagonist, 12-lipoxygenase inhibitor, protein kinase C (PKC) inhibitor, PDE IV inhibitor and the like.

2-Naphthylacetonitrile can be particularly preferably used as a starting material/intermediate for producing (1R,5S)-1-(naphthalen-2-yl)-3-azabicyclo[3.1.0]hexane described in patent document 1, patent document 2, patent document 3 and the like.

As a production method of 2-naphthylacetonitrile, a method including brominating 2-methylnaphthalene to give 2-(bromomethyl)naphthalene, and reacting same with sodium cyanide (patent document 4), and a method including reacting 2'-acetonaphthone with iodic acid or titanium tetranitrate, and trimethoxymethane to give 2-naphthylacetonitrile (non-patent document 1) are known. However, these methods are not preferable as industrial production methods since the yield is low, many by-products are generated, the reaction does not proceed sufficiently, heat is generated during the reaction, highly toxic compounds are used and the like.

In addition, a method including obtaining 2-(hydroxymethyl)naphthalene from 2-methylnaphthalene by a biochemical reaction using an enzyme and the like, and reacting same with methanesulfonyl chloride and sodium cyanide to give 2-naphthylacetonitrile (non-patent document 2) is known. However, this method is not preferable as an industrial production method since the yield is low, many by-products are generated, highly toxic compounds are used and the like.

Furthermore, some methods for synthesizing a nitrile compound from aromatic carboxylic acid, aromatic carboxylic acid derivative and the like have been reported (patent document 5, non-patent document 3, non-patent document 4 etc.). However, these methods require further improvement as industrial production methods since the yield is low, many by-products are generated, the reaction does not proceed sufficiently and the like.

Moreover, some methods for synthesizing aromatic carboxylic acid and aromatic thioamide from aromatic ketone by Willgerodt reaction have been reported (non-patent document 5, non-patent document 6, non-patent document 7 and non-patent document 8, etc.). However, these methods require further improvement as industrial production methods since the yield is not sufficient and the resulting aromatic carboxylic acid and the like are considered to contain much sulfur due to the use of sulfur in Willgerodt reaction.

DOCUMENT LIST

Patent Documents patent document 1: WO 2007/016155 patent document 2: WO 2015/089111 patent document 3: WO 2015/102826 patent document 4: JP-A-2001-39904 patent document 5: WO 2014/001939

Non-Patent Documents non-patent document 1: ARKIVOC 2011 (V) pp. 67-75 non-patent document 2: Journal of Molecular Catalysis B: Enzymatic, 6(1-2) 234-240, 2010 non-patent document 3: Tetrahedron Letters, Vol. 23, No. 14, pp 1505-1508, 1982 non-patent document 4: Organic Process Research & Development 2003, 7, 74-81 non-patent document 5: Green Chemistry Letters and Reviews, 2010, 315-318 non-patent document 6: Synthetic Communications, Vol. 33, No. 1, pp. 59-63, 2003 non-patent document 7: Chem. Soc. Rev., 2013, 42, 7870-7880 non-patent document 8: J. Soc. Ouest-Afr. Chim. (2010) 029, 89-94

SUMMARY OF INVENTION

Technical Problem

The present invention provides a method for industrially producing a highly pure aromatic nitrile compound and a highly pure aromatic carboxylic acid compound safely and highly efficiently at low costs.

Solution to Problem

In an attempt to solve the aforementioned problems, the present inventors have conducted intensive studies of production of aromatic carboxylic acid compound by Willgerodt rearrangement using comparatively economical and general aromatic ketone compounds such as 2'-acetonaphthone and the like, and further, production of a highly pure aromatic nitrile compound in a high yield from an aromatic carboxylic acid compound while suppressing generation of by-products, and arrived at the present invention.

That is, the gist of the present invention is as follows.

[1] A method for producing a nitrile compound represented by the formula (1)

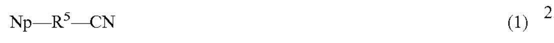

$Np—R^5—CN$ (1)

wherein, in the formula (1), Np is a naphthyl group optionally having substituent(s), and $R^5$ is an alkylene group having 1-3 carbon atoms, comprising the following step 1 and step 2:

step 1:

a step of subjecting a compound represented by the formula (2)

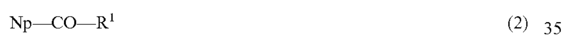

$Np—CO—R^1$ (2)

wherein, in the formula (2), Np is as defined above, and $R^1$ is an alkyl group having 1-3 carbon atoms, to Willgerodt reaction in the presence of an additive as necessary to give a compound represented by the formula (3)

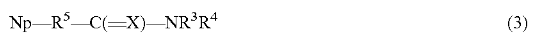

$Np—R^5—C(═X)—NR^3R^4$ (3)

wherein, in the formula (1), Np and $R^5$ are as defined above, X is an oxygen atom or a sulfur atom, $R^3$ and $R^4$ are each independently an alkyl group having 1-3 carbon atoms and optionally having a nitrogen atom, an oxygen atom or a sulfur atom, or a hydrogen atom, and $R^3$ and $R^4$ are optionally bonded to form a ring, and hydrolyzing and thereafter neutralizing the obtained compound to give a carboxylic acid compound represented by the formula (4)

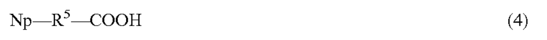

$Np—R^5—COOH$ (4)

wherein, in the formula (4), Np and $R^5$ are as defined above;

step 2: Step 2A or Step 2B step 2A:

a step of reacting the carboxylic acid compound represented by the aforementioned formula (4), obtained in the aforementioned step 1, with a halogenating agent in the presence of a catalyst as necessary in an organic solvent, further reacting the obtained compound with an amidating agent to give a compound represented by the formula (5)

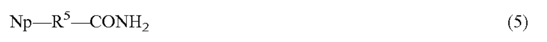

$Np—R^5—CONH_2$ (5)

wherein, in the formula (5), Np and $R^5$ are as defined above, or the formula (6)

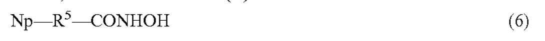

$Np—R^5—CONHOH$ (6)

wherein, in the formula (6), Np and $R^5$ are as defined above, and reacting the obtained compound with a dehydrating agent to give a nitrile compound represented by the aforementioned formula (1);

step 2B:

a step of reacting the carboxylic acid compound represented by the aforementioned formula (4), obtained in the aforementioned step 1, with a halogenating agent and a compound represented by the formula (7)

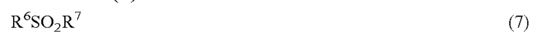

$R^6SO_2R^7$ (7)

wherein, in the formula (7), $R^6$ and $R^7$ are each independently a chlorine atom, a hydroxyl group, an amino group, an isocyanate group or a p-tolyl group, in the presence of a catalyst as necessary in an organic solvent to give a nitrile compound represented by the aforementioned formula (1).

[2] The method for producing a nitrile compound of [1], wherein the aforementioned step 2B is the following step 2B-1 or step 2B-2:

step 2B-1:

a step of reacting the carboxylic acid compound represented by the aforementioned formula (4) with a halogenating agent and a compound represented by the aforementioned formula (7) in the presence of a catalyst as necessary in an organic solvent at 80° C.-180° C. to give a nitrile compound represented by the aforementioned formula (1);

step 2B-2:

a step of reacting reaction starting material 1 which is a mixture of the carboxylic acid compound represented by the aforementioned formula (4), a halogenating agent, a first organic solvent and, where necessary, a catalyst, with reaction starting material 2 which is a mixture of a compound represented by the aforementioned formula (7) and a second organic solvent at 80° C.-180° C. to give a nitrile compound represented by the aforementioned formula (1).

[3] A method for producing a nitrile compound represented by the formula (1)

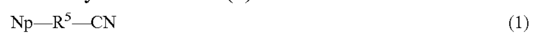

$Np—R^5—CN$ (1)

wherein, in the formula (1), Np is a naphthyl group optionally having substituent(s), and $R^5$ is an alkylene group having 1-3 carbon atoms, comprising the following step 2A or step 2B:

step 2A:

a step of reacting a carboxylic acid compound represented by the formula (4)

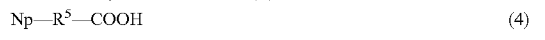

$Np—R^5—COOH$ (4)

wherein, in the formula (4), Np and $R^5$ are as defined above, with a halogenating agent in the presence of a catalyst as necessary in an organic solvent, further reacting the obtained compound with an amidating agent to give a compound represented by the formula (5)

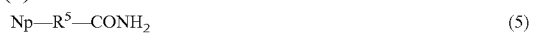

$Np—R^5—CONH_2$ (5)

wherein, in the formula (5), Np and $R^5$ are as defined above, or the formula (6)

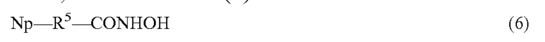

$Np—R^5—CONHOH$ (6)

wherein, in the formula (6), Np and $R^5$ are as defined above, and reacting the obtained compound with a dehydrating agent to give a nitrile compound represented by the aforementioned formula (1);

step 2B:

a step of reacting a carboxylic acid compound represented by the formula (4)

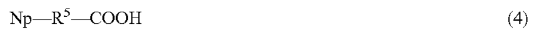

Np—$R^5$—COOH (4)

wherein, in the formula (4), Np and $R^5$ are as defined above, with a halogenating agent and a compound represented by the formula (7)

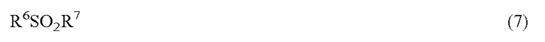

$R^6SO_2R^7$ (7)

wherein, in the formula (7), $R^6$ and $R^7$ are each independently a chlorine atom, a hydroxyl group, an amino group, an isocyanate group or a p-tolyl group, in the presence of a catalyst as necessary in an organic solvent to give a nitrile compound represented by the aforementioned formula (1).

[4] The method for producing a nitrile compound of [3], wherein the step 2B is the following step 2B-1 or step 2B-2:

step 2B-1:

a step of reacting a carboxylic acid compound represented by the aforementioned formula (4) with a halogenating agent and a compound represented by the aforementioned formula (7) in the presence of a catalyst as necessary in an organic solvent at 80° C.-180° C. to give a nitrile compound represented by the aforementioned formula (1);

Step 2B-2:

a step of reacting reaction starting material 1 which is a mixture of a carboxylic acid compound represented by the aforementioned formula (4), a halogenating agent, a first organic solvent and, where necessary, a catalyst, with reaction starting material 2 which is a mixture of a compound represented by the aforementioned formula (7) and a second organic solvent at 80° C.-180° C. to give a nitrile compound represented by the aforementioned formula (1).

[5] A method for producing a carboxylic acid compound represented by the formula (4)

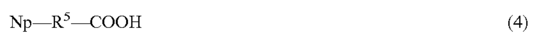

Np—$R^5$—COOH (4)

wherein, in the formula (4), Np is a naphthyl group optionally having substituent(s), and $R^5$ is an alkylene group having 1-3 carbon atoms, comprising subjecting a compound represented by the formula (2)

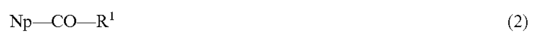

Np—CO—$R^1$ (2)

wherein, in the formula (2), Np is as defined above, and $R^1$ is an alkyl group having 1-3 carbon atoms, to Willgerodt reaction in the presence of an additive as necessary to give a compound represented by the formula (3)

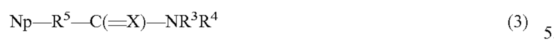

Np—$R^5$—C(═X)—$NR^3R^4$ (3)

wherein, in the formula (1), Np and $R^5$ are as defined above, X is an oxygen atom or a sulfur atom, $R^3$ and $R^4$ are each independently an alkyl group having 1-3 carbon atoms and optionally having a nitrogen atom, an oxygen atom or a sulfur atom, or a hydrogen atom, and $R^3$ and $R^4$ are optionally bonded to form a ring, and hydrolyzing and thereafter neutralizing the obtained compound.

[6] The method for producing a carboxylic acid compound of [5], wherein, after the aforementioned hydrolysis, the reaction product obtained by the hydrolysis is contacted with a hydrocarbon solvent; a hydrocarbon solvent is present during the aforementioned neutralization; or the reaction product obtained by the aforementioned neutralization is contacted with a hydrocarbon solvent.

[7] A carboxylic acid compound represented by the formula (4)

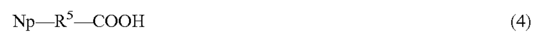

Np—$R^5$—COOH (4)

wherein, in the formula (4), $R^5$ is an alkylene group having 1-3 carbon atoms, and Np is a naphthyl group optionally having substituent(s), said compound has a sulfur content of 0.001 mol %-1 mol %, and a purity of not less than 98 mol %.

Advantageous Effects of Invention

The present invention can provide a novel method for industrially producing highly pure aromatic nitrile compounds such as 2-naphthylacetonitrile and the like and highly pure aromatic carboxylic acid compounds such as 2-naphthylacetic acid and the like, that are useful as starting materials for synthesis, or intermediates for synthesis of various pharmaceutical products, agricultural chemicals, and chemical products, safely and highly efficiently at low costs. Furthermore, using the thus-obtained aromatic nitrile compounds such as 2-naphthylacetonitrile and the like, pharmaceutical products such as (1R,5S)-1-(naphthalen-2-yl)-3-azabicyclo[3.1.0]hexane and the like can be produced safely at low costs.

DESCRIPTION OF EMBODIMENTS

Figure 1:
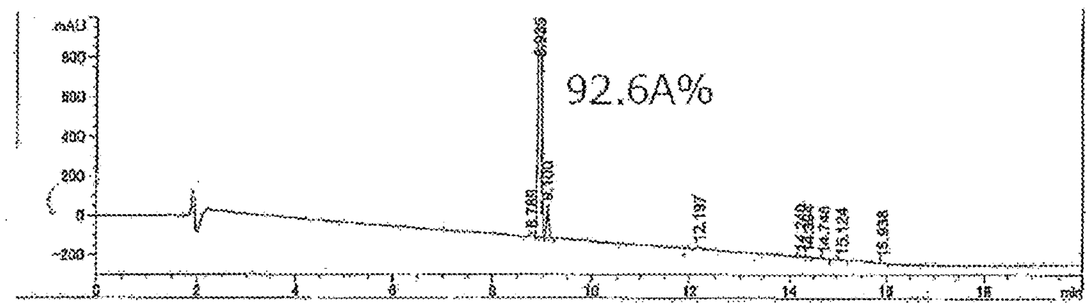
FIG. 1 shows the HPLC analysis results of crude crystals of the carboxylic acid compound obtained in Example 1.

The terms used in the present specification are explained below.

In the present specification, Np is a naphthyl group optionally having substituent(s). The naphthyl group is, for example, a 1-naphthyl group or a 2-naphthyl group, preferably a 2-naphthyl group. The substituent that Np optionally has is a halogen atom (e.g., a chlorine atom, a bromine atom), a linear or branched alkyl group having 1-6 carbon atoms (e.g., a methyl group, an ethyl group), a linear or branched alkoxy group having 1-6 carbon atoms (e.g., a methoxy group, an ethoxy group) or the like. Np is particularly preferably a 2-naphthyl group.

In the present specification, $R^1$ is a linear or branched alkyl group having 1-3 carbon atoms. Preferably, $R^1$ is an alkyl group having 1-2 carbon atoms, particularly preferably methyl group.

In the present specification, $R^3$ and $R^4$ are each independently a linear or branched alkyl group having 1-3 carbon atoms and optionally having a nitrogen atom, an oxygen atom or a sulfur atom, or a hydrogen atom. In addition, $R^3$ and $R^4$ may be bonded to form a ring. Preferably, $R^3$ and $R^4$ are each independently alkyl having 1-2 carbon atoms and optionally having an oxygen atom, and $R^3$ and $R^4$ are bonded to form a ring. Particularly, $—NR^3R^4$ is preferably a morpholino group.

In the present specification, X is an oxygen atom or a sulfur atom.

In the present specification, $R^5$ is an alkylene group having 1-3 carbon atoms. Preferably, $R^5$ is an alkylene group having 1-2 carbon atoms, particularly preferably a methylene group.

In the present specification, $R^6$ and $R^7$ are each independently a chlorine atom, a hydroxyl group, an amino group, an isocyanate group or a p-tolyl group. Preferably, $R^6$ is an amino group or an isocyanate group and $R^7$ is a hydroxyl group, an amino group or a chlorine atom. Particularly preferably, $R^6$ and $R^7$ are amino groups, $R^6$ is an amino group and $R^7$ is a hydroxyl group, or $R^6$ is an isocyanate group and $R^7$ is a chlorine atom.

In the present specification, Z is a halogen atom. Preferably, it is a bromine atom or a chlorine atom, particularly preferably a chlorine atom.

The present invention is described in detail below.

1. Step 1

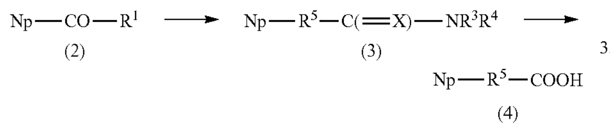

In step 1, a compound represented by the formula (2) is subjected to Willgerodt reaction in the presence of an additive as necessary, and then the obtained amide compound represented by the formula (3) is hydrolyzed and neutralized to obtain a carboxylic acid compound represented by the formula (4).

In the present specification, Willgerodt reaction means Willgerodt reaction and Willgerodt-Kindler reaction.

As the compound represented by the formula (2), 2'-acetonaphthone is particularly preferable.

The Willgerodt reaction can be performed by reacting a compound represented by the formula (2) with a sulfur compound such as sodium sulfide ($Na_2S·9H_2O$), ammonium sulfide ($(NH_4)_2S$) and the like under heating. As the sulfur compound, one kind may be used alone, or two or more kinds may be used in any combination and ratio. The reaction can be performed in the presence of an aqueous solvent such as water and the like.

The amount of the sulfur compound to be used is not particularly limited as long as it is an amount effective for the Willgerodt reaction of the compound represented by the formula (2). The amount of the sulfur compound to be used is generally 1 mol-5 mol, preferably 1 mol-3 mol, per 1 mol of the compound represented by the formula (2).

The reaction temperature is generally 90° C.-150° C., preferably 100° C.-140° C., particularly preferably 110° C.-130° C. The reaction is generally performed under normal pressure.

The reaction time can be appropriately determined according to the progress of the reaction and is generally 1 hr-12 hr, preferably 2 hr-10 hr.

The Willgerodt reaction in the present invention can be performed by reacting a compound represented by the formula (2) with sulfur and secondary amine such as dialkyl amine, morpholine and the like under heating (Willgerodt-Kindler reaction).

The amount of sulfur to be used is not particularly limited as long as it is an amount effective for the Willgerodt-Kindler reaction of the compound represented by the formula (2). The amount of the sulfur to be used is generally 1 mol-5 mol, preferably 1 mol-3 mol, per 1 mol of the compound represented by the formula (2).

The secondary amine for industrial production is preferably morpholine since reaction without solvent can be performed efficiently.

The amount of the secondary amine to be used is not particularly limited as long as it is an amount effective for the Willgerodt-Kindler reaction of the compound represented by the formula (2). The amount of the secondary amine to be used is generally 2 mol-6 mol, preferably 2 mol-4 mol, per 1 mol of the compound represented by the formula (2).

The reaction can be performed without solvent or in an organic solvent inert to the reaction. Examples of the organic solvent include dioxane, water, dimethylformamide and the like. As these organic solvents, one kind may be used alone, or two or more kinds may be used in any combination and ratio.

The reaction temperature is generally 90° C.-150° C., preferably 100° C.-140° C., particularly preferably 110° C.-130° C. The reaction is generally performed under normal pressure.

The reaction time can be appropriately determined according to the progress of the reaction and is generally 1 hr—not less than 12 hr, preferably 2 hr-10 hr.

When performing the Willgerodt reaction, additives may also be used as necessary. Examples of the additive include dehydrating agents such as zeolite, molecular sieves, magnesium sulfate, sodium sulfate and the like. As the dehydrating agent, one kind may be used alone, or two or more kinds may be used in any combination and ratio. The reaction can proceed efficiently by controlling the amount of water in the reaction system to a low level. The amount of the dehydrating agent to be used is generally 1 mol-5 mol, preferably 1.5 mol-4 mol, per 1 mol of the compound represented by the formula (2).

Examples of the additive include organic acids such as p-toluenesulfonic acid, methanesulfonic acid, oxalic acid, trifluoroacetic acid and the like. As the organic acid, one kind may be used alone, or two or more kinds may be used in any combination and ratio. As the organic acid, p-toluenesulfonic acid or methanesulfonic acid is particularly preferable. Using these organic acids as the additive, production of by-products, particularly a thiocarbamate compound represented by the following formula

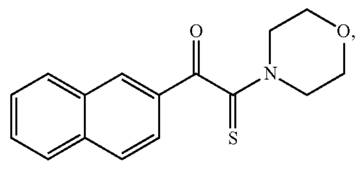 [SMILES: O=C(C(=S)N1CCOCC1)c1ccc2ccccc2c1]

is suppressed, and the reaction can proceed efficiently.

The amount of the organic acid to be used is generally 0.01 mol-5 mol, preferably 0.05 mol-3 mol, per 1 mol of the compound represented by the formula (2).

To control the amount of water in the reaction system to a low level, the reaction may be performed while dehydrating by distillation.

The amide compound represented by the formula (3) obtained by the Willgerodt reaction may be subjected to hydrolysis after separation from the reaction system, or may be subjected to the next hydrolysis without separation.

In the present invention, the amide compound represented by the formula (3) is hydrolyzed with a base. Examples of the base include alkali metal hydroxides such as sodium hydroxide, potassium hydroxide and the like; alkaline earth metal hydroxides such as calcium hydroxide and the like; alkali metal carbonates such as sodium carbonate, potassium carbonate and the like; alkaline earth metal carbonates such as calcium carbonate and the like; alkali metal hydrogen carbonates such as sodium hydrogen carbonate, potassium hydrogen carbonate and the like; alkaline earth metal hydrogen carbonates such as calcium hydrogen carbonate and the like; and alkali metal alkoxides such as sodium methoxide, sodium ethoxide, potassium methoxide, potassium ethoxide and the like. Industrially, it is preferable to use alkali metal hydroxides such as sodium hydroxide, potassium hydroxide and the like because of the cost and availability. As the base, one kind may be used alone, or two or more kinds may be used in any combination and ratio.

The amount of the base to be used is not particularly limited as long as it is an amount effective for hydrolysis of the amide compound represented by the formula (3). The amount of the base to be used is preferably 1 mol-10 mol, preferably 1 mol-5 mol, per 1 mol of the amide compound represented by the formula (3).

Hydrolysis may be performed without a solvent or in a solvent such as water and the like. It is preferably performed in a solvent in view of superior stirrability and uniformity.

The temperature of hydrolysis is not particularly limited as long as the hydrolysis proceeds. The hydrolysis temperature is generally 80° C.-115° C., preferably 85° C.-110° C.

Hydrolysis is generally performed under normal pressure.

The reaction product obtained by hydrolysis (e.g., sodium 2-naphthylacetate) is neutralized to obtain a carboxylic acid compound represented by the formula (4). Acids such as hydrochloric acid, sulfuric acid, hydrobromic acid and the like can be used for neutralization. As the acid, one kind may be used alone, or two or more kinds may be used in any combination and ratio. Industrially, hydrochloric acid is preferable because of the reaction efficiency, cost and the like.

The amount of the acid to be used is not particularly limited as long as it is an amount effective for neutralization. The amount of the acid to be used is preferably 1 mol-20 mol, preferably 3 mol-10 mol, per 1 mol of the reaction product obtained by hydrolysis.

The pH at the end-point of neutralization is generally between 0 and 5.

The neutralization temperature is not particularly limited as long as the neutralization proceeds. The neutralization temperature is generally 10° C.-80° C., preferably 20° C.-50° C.

The reaction product obtained by neutralization may be washed once or multiple times with an appropriate washing solution such as water, an aqueous solution and the like.

The carboxylic acid compound represented by the formula (4) can be extracted and recovered using an organic solvent from the reaction product obtained by neutralization. Examples of the organic solvent include hydrocarbon solvents capable of dissolving the carboxylic acid compound represented by the formula (4). Preferable examples of the hydrocarbon solvent include alicyclic hydrocarbon solvents such as cyclohexane, methylcyclohexane and the like; and aromatic hydrocarbon solvents such as benzene, toluene, xylene, mesitylene, ethylbenzene, tert-butylbenzene, trifluoromethylbenzene, nitrobenzene, chlorobenzene, chlorotoluene, bromobenzene and the like. The hydrocarbon solvent may be used alone, or two or more kinds may be used in any combination and ratio. The hydrocarbon solvent is particularly preferably cyclohexane, toluene, xylene or chlorobenzene.

For example, an organic solvent (e.g., toluene, xylene, cyclohexane, chlorobenzene, etc.) capable of dissolving the carboxylic acid compound represented by the formula (4) is added to the reaction product obtained by neutralization, the mixture is stirred under acidic conditions (e.g., not more than pH3) with heating (e.g., 50° C.-90° C.), and washing, separation of the aqueous layer, concentration and the like are conducted as necessary, and after cooling, the carboxylic acid compound represented by the formula (4) can be precipitated and recovered as a solid.

Since sulfur or sulfur compound is used in the Willgerodt reaction, the obtained reaction product generally contains several mol % or more of sulfur. Sulfur is an impurity for the carboxylic acid compound represented by the formula (4), which is the target product of step 1. When a chemical reaction or the like is performed using the carboxylic acid compound represented by the formula (4) as a starting material, sulfur may decrease the reaction efficiency. Accordingly, it is preferable to remove sulfur as much as possible.

In the present invention, the sulfur content of the carboxylic acid compound represented by the formula (4) obtained in step 1 can be decreased by contacting same with a hydrocarbon solvent after the aforementioned hydrolysis, performing the aforementioned neutralization in the presence of a hydrocarbon solvent, or contacting the reaction product obtained by the aforementioned neutralization with a hydrocarbon solvent. Water, an aqueous solution or the like may be present as necessary when contacting the compound with a hydrocarbon solvent.

The hydrocarbon solvent is preferably an alicyclic hydrocarbon solvent such as cyclohexane, methylcyclohexane or the like; or an aromatic hydrocarbon solvent such as benzene, toluene, xylene, mesitylene, ethylbenzene, tert-butylbenzene, trifluoromethylbenzene, nitrobenzene, chlorobenzene, chlorotoluene, bromobenzene or the like, more preferably toluene, xylene or chlorobenzene, particularly preferably toluene.

When contacting with a hydrocarbon solvent after the aforementioned hydrolysis, the hydrocarbon solvent is added to the reaction product obtained by the hydrolysis reaction, or the reaction product obtained by the hydrolysis reaction is added to the hydrocarbon solvent. In this case, water, an aqueous solution or the like may be added as necessary.

The hydrocarbon solvent is used at generally 1-20 volume ratio, preferably 1.5-10 volume ratio, particularly preferably 3-5 volume ratio, to the carboxylic acid compound represented by the formula (4).

The contact temperature is generally 50° C.-90° C., preferably 60° C.-80° C. The contact time is generally 10 min-5 hr, preferably 30 min-2 hr.

Thereafter, the hydrocarbon solvent layer is removed by partitioning or the like, and the aqueous layer containing the reaction product obtained by the hydrolysis reaction is subjected to the neutralization reaction.

When a hydrocarbon solvent is present during the aforementioned neutralization, an acid and a hydrocarbon solvent are added to the reaction product obtained by the hydrolysis reaction, or the reaction product obtained by the hydrolysis reaction is added to a mixture of an acid and a hydrocarbon solvent to perform a neutralization reaction. In this case, water, an aqueous solution, or the like may be added as necessary.

The hydrocarbon solvent is used at generally 1-30 volume ratio, preferably 3-20 volume ratio, particularly preferably 5-15 volume ratio, to the carboxylic acid compound represented by the formula (4).

After the neutralization reaction, the aqueous layer is removed by partitioning or the like to obtain an organic layer containing a carboxylic acid compound represented by the formula (4). The obtained organic layer may be washed once or multiple times with an appropriate washing solution such as water, an aqueous solution and the like.

When a hydrocarbon solvent is contacted with the reaction product obtained by the aforementioned neutralization, the hydrocarbon solvent is added to the reaction product obtained by the neutralization, or the reaction product obtained by the neutralization is added to the hydrocarbon solvent. In this case, water, an aqueous solution or the like may be added as necessary.

The hydrocarbon solvent is used at generally 1-20 volume ratio, preferably 1.5-10 volume ratio, particularly preferably 3-5 volume ratio, to the carboxylic acid compound represented by the formula (4).

The contact temperature is generally 50° C.-90° C., preferably 60° C.-80° C. The contact time is generally 10 min-5 hr, preferably 30 min-2 hr. Furthermore, the contact is preferably performed under acidic conditions of not more than pH 3, preferably not more than pH 2.

Thereafter, the aqueous layer is removed by partitioning or the like to obtain an organic layer containing a carboxylic acid compound represented by the formula (4). The obtained organic layer may be washed once or multiple times with an appropriate washing solution such as water, an aqueous solution and the like. The obtained organic layer is concentrated as necessary and cooled, whereby the carboxylic acid compound represented by the formula (4) can be precipitated and recovered as a solid.

In the present invention, toluene is particularly preferable as the aforementioned hydrocarbon solvent because the removal of sulfur and the extraction of the carboxylic acid compound represented by the formula (4) can be performed with a single solvent.

As described above, the carboxylic acid compound represented by the formula (4) obtained by contacting with a hydrocarbon solvent or the like in step 1 of the present invention has high quality with a sulfur content of 0.001 mol %-1 mol %, preferably 0.001 mol %-0.5 mol %, and a purity of not less than 98 mol %, preferably not less than 99 mol %.

The carboxylic acid compound represented by the formula (4) obtained in step 1 is useful as a starting material for synthesis, or an intermediate for synthesis of various industrial products, pharmaceutical products and the like, and can be subjected to step 2 of the present invention.

2. Step 2

In step 2, a nitrile compound represented by the aforementioned formula (1) is obtained from a carboxylic acid compound represented by the aforementioned formula (4).

Step 2 may be any of the following step 2A and step 2B.

The carboxylic acid compound represented by the formula (4) may be commercially available or one obtained in the aforementioned step 1 can be used. As the carboxylic acid compound represented by the formula (4), 2-naphthylacetic acid is particularly preferable.

(1) Step 2A

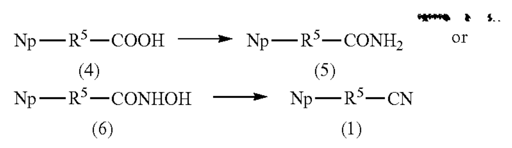

In step 2A, the carboxylic acid compound represented by the formula (4) is reacted with a halogenating agent in the presence of a catalyst as necessary in an organic solvent, further reacted with an amidating agent and the obtained compound represented by the formula (5) or the formula (6) is reacted with a dehydrating agent to give a nitrile compound represented by the aforementioned formula (1).

First, the carboxylic acid compound represented by the formula (4) is reacted with a halogenating agent in the presence of a catalyst as necessary (acid halogenation).

The halogenating agent is not particularly limited as long as it can halogenate the carboxylic acid compound represented by the aforementioned formula (4). As the halogenating agent, a chlorinating agent and a brominating agent are preferable, and a chlorinating agent is more preferable. Examples of the chlorinating agent include thionyl chloride, oxalyl chloride, sulfuryl chloride, phosphoryl chloride, phosphorus trichloride, phosphorus pentachloride and the like, and examples of the brominating agent include thionyl bromide, phosphorus tribromide and the like. As the halogenating agent, one kind may be used alone, or two or more kinds may be used in any combination and ratio. Among these, thionyl chloride, phosphoryl chloride, phosphorus pentachloride, thionyl bromide, and phosphorus tribromide are preferable, and thionyl chloride is particularly preferable, from the aspects of cost, broad utility, reactivity, and the like.

The amount of the halogenating agent to be used is not particularly limited as long as it is an amount effective for acid halogenation. It is preferably 1 mol-5 mol, more preferably 1 mol-3 mol, particularly preferably 1 mol-2 mol, per 1 mol of the carboxylic acid compound represented by the formula (4).

The organic solvent is not particularly limited as long as the reaction proceeds, and examples thereof include ester solvent, ether solvent, ketone solvent, nitrile solvent, amide solvent, sulfoxide solvent, hydrocarbon solvent, and basic organic solvent. As the organic solvent, one kind may be used alone, or two or more kinds may be used in any combination and ratio.

Among these, the organic solvent is preferably a hydrocarbon solvent, and alicyclic hydrocarbon solvents such as cyclohexane, methylcyclohexane and the like; and aromatic hydrocarbon solvents such as benzene, toluene, xylene, mesitylene, ethylbenzene, tert-butylbenzene, trifluoromethylbenzene, nitrobenzene, chlorobenzene, chlorotoluene, bromobenzene and the like are preferable. Particularly, toluene, xylene and chlorobenzene are preferable from the aspects of cost, broad utility, reactivity, and the like.

A catalyst may be present to accelerate the reaction during acid halogenation. The catalyst is not particularly limited as long as it promotes the reaction between the carboxylic acid compound represented by the formula (4) and the halogenating agent. Examples of the catalyst include N,N-dimethylformamide, N-methylpyrrolidone, N,N-dimethylacetamide and the like, and N,N-dimethylformamide is particularly preferable.

The amount of the catalyst to be used is not particularly limited as long as it is an amount effective for functioning as a catalyst. The amount of the catalyst to be used is preferably 0.0001 mol-1 mol, particularly preferably 0.001 mol-0.1 mol, per 1 mol of the carboxylic acid compound represented by the formula (4).

The temperature of the acid halogenation is generally 20° C.-60° C., preferably 30° C.-50° C., from the aspects of productivity and the like. The reaction time can be appropriately determined according to the progress of the reaction and is generally 0.5 hr-10 hr, preferably 1 hr-5 hr. The reaction is generally performed under normal pressure.

The obtained acid halogenation solution can be directly subjected to the next amidation step.

The acid halogenation solution obtained as described above is reacted with an amidating agent to obtain an amide compound represented by the formula (5) or the formula (6).

Examples of the amidating agent include ammonia (gas, aqueous solution) and hydroxyamine. As the amidating agent, ammonia (gas, aqueous solution) is preferable from the aspects of cost, broad utility, reactivity and the like.

When ammonia (gas, aqueous solution) is used as the amidating agent, the amide compound represented by the formula (5) is obtained, and when hydroxyamine is used, the amide compound represented by the formula (6) is obtained.

The amount of the amidating agent to be used is not particularly limited as long as it is an amount at which amidation is possible. It is preferably 1 mol-20 mol, preferably 2 mol-10 mol, per 1 mol of the carboxylic acid compound represented by the formula (4) from the aspects of cost, reactivity and the like.

In the amidation reaction, an amidating agent may be added to the aforementioned acid halogenation solution, or the aforementioned acid halogenation solution may be added to the amidating agent. Where necessary, a solvent such as water, an organic solvent or the like that does not inhibit the amidation reaction may be present.

The temperature of the amidation reaction is generally 20° C.-60° C., preferably 30° C.-50° C., from the aspects of productivity and the like. The reaction time can be appropriately determined according to the progress of the reaction and is generally 0.5 hr-10 hr, preferably 1 hr-5 hr. The reaction is generally performed under normal pressure.

When ammonia gas is used as the amidating agent, the ammonia gas may be supplied by purging into the gaseous phase part of the reactor, or may be supplied by depressurizing the reactor and then repressurizing the reactor with ammonia gas, or may be supplied by bubbling ammonia gas in the reaction mixture. In this case, the temperature is generally 10° C.-80° C., preferably 20° C.-70° C., from the aspects of productivity and the like.

When ammonia gas is used as the amidating agent, moreover, it is preferable to reduce, before the reaction with the dehydrating agent, the ammonia gas contained in the amidation reaction mixture obtained by amidation. As a result, the amount of the dehydrating agent to be used next can be reduced, the operability can be improved, the production of by-products can be suppressed, and the cost can be reduced.

Examples of the method for reducing the ammonia gas contained in the reaction mixture include heating the reaction mixture, purging the gaseous phase part in the reactor with nitrogen, and setting the inside of the reactor under a reduced pressure condition.

The amide compound represented by the formula (5) or the formula (6) obtained as described above is reacted with a dehydrating agent (dehydration cyanation) to obtain a nitrile compound represented by the aforementioned formula (1).

The amide compound represented by the formula (5) or the formula (6) may be directly subjected to a reaction with a dehydrating agent, or may be once isolated, purified or the like and then subjected to a reaction with a dehydrating agent.

Examples of the dehydrating agent include phosphorus dehydrating agent, chlorine dehydrating agent, and nitrogen dehydrating agent. Specifically, phosphorus pentoxide, polyphosphoric acid, phosphorus pentachloride, thionyl chloride, phosphoryl chloride, acetyl chloride, tosyl chloride/pyridine, cyanuric chloride, benzenesulfonyl chloride, oxalyl chloride, phosphorus tribromide and the like can be mentioned. As the dehydrating agent, one kind may be used alone, or two or more kinds may be used in any combination and ratio.

As the dehydrating agent, phosphorus pentoxide, phosphoryl chloride, cyanuric chloride, and phosphorus tribromide are preferable from the aspects of cost, reactivity and the like.

The amount of the dehydrating agent to be used is not particularly limited as long as it is an amount at which dehydration cyanation is possible. It is preferably 0.1 mol-10 mol, preferably 0.5 mol-10 mol, per 1 mol of the aforementioned amide compound from the aspects of cost, reactivity and the like.

In the reaction between the amide compound and the dehydrating agent, a dehydrating agent may be added to the aforementioned amidation reaction mixture, or the aforementioned amidation reaction mixture may be added to the dehydrating agent. Where necessary, a solvent such as water, an organic solvent or the like that does not inhibit the dehydration cyanation reaction may be present.

The reaction temperature is generally 20° C.-120° C., preferably 50° C.-110° C., particularly preferably 70° C.-100° C., from the aspects of productivity and the like. The reaction time can be appropriately determined according to the progress of the reaction and is generally 0.5 hr-10 hr, preferably 1 hr-8 hr. The reaction is generally performed under normal pressure.

The thus-obtained nitrile compound represented by the aforementioned formula (1) can be extracted and recovered using an organic solvent from the dehydration cyanation reaction product. For example, the dehydration cyanation reaction product and an organic solvent (e.g., toluene, ethyl acetate, tert-butyl methyl ether etc.) capable of dissolving the nitrile compound represented by the formula (1) are mixed, and washing, separation of the aqueous layer, concentration and the like are conducted as necessary, and after cooling, the nitrile compound represented by the formula (1) can be precipitated and recovered as a solid.

In step 2A, the amide compound represented by the formula (5) or the formula (6) is easy to crystallize, and thus a highly pure amide compound can be easily isolated and recovered. In addition, using the highly pure amide compound, a nitrile compound represented by the aforementioned formula (1) with high purity and high quality can be obtained.

(2) Step 2B

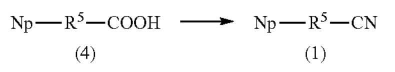

(4) (1)

In step 2B, a carboxylic acid compound represented by the aforementioned formula (4) is reacted with a halogenating agent and a compound represented by the following formula (7)

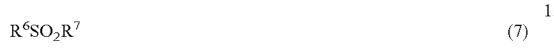

$R^6SO_2R^7$ (7)

in the presence of a catalyst as necessary in an organic solvent to obtain a nitrile compound represented by the aforementioned formula (1).

As the compound represented by the formula (7), sulfamide, sulfamic acid or chlorosulfonyl isocyanate is particularly preferable.

The desired nitrile compound represented by the formula (1) can be purified by crystallizing with an organic solvent such as toluene, heptane or the like.

In addition, the desired nitrile compound represented by the formula (1) can be precipitated as crystals by adding water to the reaction mixture containing the nitrile compound.

Step 2B is industrially preferable since it can be performed in a single reactor.

In step 2B, high quality nitrile compound represented by the formula (1) with a purity (HPLC) of preferably not less than 98 Area %, particularly preferably not less than 99 Area %, can be obtained.

Specifically, step 2B may any of the following step 2B-1 and step 2B-2.

Step 2B-1:

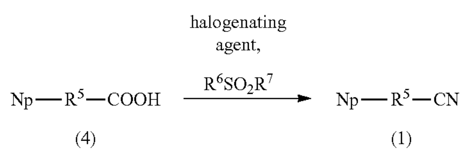

(4) (1)

In step 2B-1, a carboxylic acid compound represented by the aforementioned formula (4) is reacted with a halogenating agent and a compound represented by the formula (7) in the presence of a catalyst as necessary in an organic solvent at 80° C.-180° C. to give a nitrile compound represented by the aforementioned formula (1).

The halogenating agent is not particularly limited as long as it can halogenate the carboxylic acid compound represented by the aforementioned formula (4). As the halogenating agent, a chlorinating agent and a brominating agent are preferable, and a chlorinating agent is more preferable. Examples of the chlorinating agent include thionyl chloride, oxalyl chloride, sulfuryl chloride, phosphoryl chloride, phosphorus trichloride, phosphorus pentachloride and the like, and examples of the brominating agent include thionyl bromide, phosphorus tribromide and the like. As the halogenating agent, one kind may be used alone, or two or more kinds may be used in any combination and ratio. Among these, thionyl chloride, phosphoryl chloride, phosphorus pentachloride, thionyl bromide, and phosphorus tribromide are preferable, and thionyl chloride is particularly preferable, from the aspects of cost, broad utility, reactivity, and the like.

The amount of the halogenating agent to be used is not particularly limited as long as it is an amount at which a carboxylic acid compound represented by the aforementioned formula (4) can be halogenated. For sufficient halogenation of the carboxylic acid compound, not less than 1 mol of the halogenating agent is preferably used per 1 mol of the carboxylic acid compound.

While the upper limit is not particularly set on the amount to be used, not more than 3 mol per 1 mol of the carboxylic acid compound is preferable from the aspects of cost, productivity and the like. That is, the amount of the halogenating agent to be used is 1 mol-3 mol, more preferably 1.02 mol-2 mol, particularly preferably 1.05 mol-1.5 mol, per 1 mol of the carboxylic acid compound. The halogenating agent is preferably used in a slightly larger amount than the theoretical amount in order to complete the reaction.

The amount of the compound represented by the aforementioned formula (7) to be used is not particularly limited as long as it is an amount at which an acid halide compound represented by the formula (8)

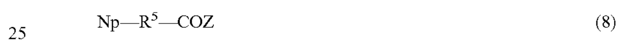

Np—$R^5$—COZ (8)

wherein, in the formula (8), Z is a halogen atom, and Np and $R^5$ are as defined above, which is produced by the reaction of the carboxylic acid compound represented by the aforementioned formula (4) and the halogenating agent, can be cyanated. Generally, it is preferably not less than 1 mol per 1 mol of the acid halide compound. The amount of the compound represented by the aforementioned formula (7) to be used is 1 mol-3 mol, more preferably 1.02 mol-2 mol, particularly preferably 1.05 mol-1.5 mol, per 1 mol of the carboxylic acid compound.

In step 2B-1, the amount of the compound represented by the aforementioned formula (7) to be used is preferably larger than the amount of the halogenating agent to be used. From the aspects of the effect, cost and the like, the amount of the compound represented by the aforementioned formula (7) to be used is preferably 2%-20%, preferably 5%-15%, larger than the amount of the halogenating agent to be used. As a result, the desired nitrile compound represented by the aforementioned formula (1) can be obtained in a high yield. When the amount of the compound represented by the aforementioned formula (7) to be used is less than the amount of the halogenating agent to be used, many by-products may be produced and the yield of the desired nitrile compound may decrease. Furthermore, when the amount of the compound represented by the aforementioned formula (7) to be used is the same as the amount of the halogenating agent to be used, the reaction may not proceed sufficiently.

A catalyst may be present to accelerate the reaction. The catalyst is not particularly limited as long as it promotes the reaction of step 2B-1. Examples of the catalyst include N,N-dimethylformamide, N-methylpyrrolidone, N,N-dimethylacetamide and the like, and N,N-dimethylformamide is particularly preferable.

The amount of the catalyst to be used is not particularly limited as long as it is an amount effective for functioning as a catalyst. The amount of the catalyst to be used is preferably 0.0001 mol-1 mol, preferably 0.001 mol-0.1 mol, per 1 mol of the carboxylic acid compound represented by the formula (4).

The organic solvent is not particularly limited as long as the reaction in step 2B-1 proceeds. Examples of the organic solvent include ester solvent, ether solvent, ketone solvent, nitrile solvent, amide solvent, sulfoxide solvent, sulfone solvent, hydrocarbon solvent, and basic organic solvent. As the organic solvent, one kind may be used alone, or two or more kinds may be used in any combination and ratio.

As the ester solvent, acetic acid esters such as ethyl acetate, propyl acetate, butyl acetate and the like can be used.

As the ether solvent, chain ethers such as diethyl ether, di-n-butyl ether, diisopropyl ether, tert-butyl methyl ether and the like; and cyclic ethers such as cyclopentyl methyl ether, tetrahydrofuran, 2-methyltetrahydrofuran, dioxane and the like can be used.

As the ketone solvent, aliphatic ketones such as acetone, methyl ethyl ketone, methyl isobutyl ketone and the like can be used.

As the nitrile solvent, aliphatic nitriles such as acetonitrile, propanonitrile, butyronitrile, isobutyronitrile, valeronitrile, isovaleronitrile and the like; aromatic nitriles such as benzonitrile and the like can be used.

As the amide solvent, aprotic amides such as N,N-dimethylformamide, N,N-dimethylacetamide, N-methylpyrrolidinone and the like can be used.

As the sulfoxide solvent, aprotic sulfoxides such as dimethyl sulfoxide and the like can be used.

As the sulfone solvent, aprotic sulfones such as ethyl methyl sulfone, ethyl isopropyl sulfone, 3-methylsulfolane, sulfolane and the like can be used.

As the hydrocarbon solvent, aliphatic hydrocarbons such as hexane, cyclohexane, heptane, cycloheptane and the like; aromatic hydrocarbons such as toluene, xylene and the like can be used.

As the basic organic solvent, pyridine solvents such as pyridine, 2-methylpyridine, 3-methylpyridine, 4-methylpyridine, 2,6-dimethylpyridine and the like can be used.

The amount of the organic solvent to be used is generally not less than 1 L, preferably not less than 2 L, further preferably not less than 3 L, per 1 kg of the carboxylic acid compound represented by the formula (4), from the aspects of operability and the like, and the upper limit is generally not more than 50 L, preferably not more than 20 L, more preferably not more than 10 L, further preferably not more than 4.5 L, particularly preferably not more than 4 L, per 1 kg of the carboxylic acid compound represented by the formula (4), from the aspects of the operability, productivity, cost and the like.

In this step, it is preferable to use a sulfone solvent as the organic solvent from the aspects of reactivity, productivity and the like, and it is particularly preferable to use sulfolane because the yield of the desired nitrile compound is improved. The sulfone solvent is preferably used alone, but may be used in combination with other organic solvents in any ratio.

The temperature of reaction with the halogenating agent may vary depending on the organic solvent, catalyst and the like to be used. The lower limit is generally not less than 80° C., preferably not less than 85° C., particularly preferably not less than 90° C., from the aspects of quality, reactivity and the like, and the upper limit is generally not more than 180° C., preferably not more than 150° C., particularly preferably not more than 120° C., from the aspects of quality, reactivity, cost and the like.

When the reaction temperature is too low, the progress of the reaction may be delayed and the productivity may decrease, and when it is too high, many by-products may be produced and the quality of the desired nitrile compound may decrease.

The temperature of reaction with a compound represented by the aforementioned formula (7) is not particularly limited as long as the reaction proceeds. The lower limit is generally not less than 0° C., preferably not less than 10° C., more preferably not less than 15° C., from the aspects of productivity and the like, and the upper limit is generally not more than 180° C., preferably not more than 150° C., more preferably not more than 120° C., from the aspects of quality, cost and the like, particularly preferably 20° C.-110° C.

When the reaction temperature is too low, the progress of the reaction may be delayed and the productivity may decrease, and when it is too high, many by-products may be produced and the quality of the desired nitrile compound may decrease.

The reaction time may vary depending on the organic solvent, catalyst and the like to be used, and can be appropriately determined according to the progress of the reaction. It is generally 0.5 hr-30 hr, preferably 1 hr-15 hr. The reaction is generally performed under normal pressure.

In one embodiment of the present step, a carboxylic acid compound represented by the aforementioned formula (4), a halogenating agent, a compound represented by the formula (7), an organic solvent, and, where necessary, a catalyst are mixed at 20° C.-70° C., and the mixture is heated to 80° C.-180° C.

In another embodiment of the present step, a carboxylic acid compound represented by the aforementioned formula (4), a halogenating agent, a compound represented by the formula (7), an organic solvent, and, where necessary, a catalyst are mixed at 80° C.-180° C.

Furthermore, in other embodiment of the present step, a carboxylic acid compound represented by the aforementioned formula (4), a compound represented by the formula (7), an organic solvent, and, where necessary, a catalyst are mixed at 20° C.-70° C., the mixture is heated to 80° C.-180° C., and a halogenating agent is added. This embodiment is preferable because the precipitation of the sulfonamide compound, which is a reaction intermediate, can be easily suppressed.

Step 2B-2:

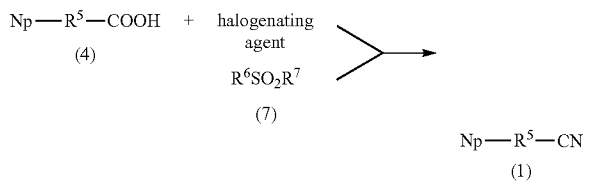

In step 2B-2, reaction starting material 1 which is a mixture of a carboxylic acid compound represented by the aforementioned formula (4), a halogenating agent, a first organic solvent and, where necessary, a catalyst, is reacted with reaction starting material 2 which is a mixture of a compound represented by the aforementioned formula (7) and a second organic solvent at 80° C.-180° C. to give a nitrile compound represented by the aforementioned formula (1).

Examples of the halogenating agent and the compound represented by the formula (7) include the same compounds as in Step 2B-1.

The amount of the halogenating agent to be used is preferably not less than 1 mol per 1 mol of the carboxylic acid compound represented by the aforementioned formula (4). In addition, use of not more than 3 mol per 1 mol of the carboxylic acid compound is preferable from the aspects of cost, productivity and the like. The amount of the halogenating agent to be used is preferably 1.02 mol-2 mol, particularly preferably 1.05 mol-1.5 mol, per 1 mol of the carboxylic acid compound. The halogenating agent is preferably used in a slightly larger amount than the theoretical amount in order to complete the reaction.

The amount of the compound represented by the aforementioned formula (7) to be used is generally preferably not less than 1 mol per 1 mol of the carboxylic acid compound represented by the aforementioned formula (4). The amount of the compound represented by the aforementioned formula (7) to be used is 1 mol-5 mol, more preferably 1.02 mol-3 mol, particularly preferably 1.05 mol-2 mol, per 1 mol of the carboxylic acid compound.

In step 2B-2, the amount of the compound represented by the aforementioned formula (7) to be used is preferably larger than the amount of the halogenating agent to be used. From the aspects of the effect, cost and the like, the amount of the compound represented by the aforementioned formula (7) to be used is preferably 2%-20%, preferably 5%-15%, larger than the amount of the halogenating agent to be used. As a result, the desired nitrile compound represented by the aforementioned formula (1) can be obtained in a high yield. When the amount of the compound represented by the aforementioned formula (7) to be used is less than the amount of the halogenating agent to be used, many by-products may be produced and the yield of the desired nitrile compound may decrease. Furthermore, when the amount of the compound represented by the aforementioned formula (7) to be used is the same as the amount of the halogenating agent to be used, the reaction may not proceed sufficiently.

The first organic solvent is not particularly limited as long as the reaction in step 2B-2 proceeds. Examples of the organic solvent include ester solvent, ether solvent, ketone solvent, nitrile solvent, amide solvent, sulfoxide solvent, sulfone solvent, hydrocarbon solvent, and basic organic solvent. As the organic solvent, one kind may be used alone, or two or more kinds may be used in any combination and ratio.

As the ester solvent, acetic acid esters such as ethyl acetate, propyl acetate, butyl acetate and the like can be used.

As the ether solvent, chain ethers such as diethyl ether, di-n-butyl ether, diisopropyl ether, tert-butyl methyl ether and the like; and cyclic ethers such as cyclopentyl methyl ether, tetrahydrofuran, 2-methyltetrahydrofuran, dioxane and the like can be used.

As the ketone solvent, aliphatic ketones such as acetone, methyl ethyl ketone, methyl isobutyl ketone and the like can be used.

As the nitrile solvent, aliphatic nitriles such as acetonitrile, propanonitrile, butyronitrile, isobutyronitrile, valeronitrile, isovaleronitrile and the like; aromatic nitriles such as benzonitrile and the like can be used.

As the amide solvent, aprotic amides such as N,N-dimethylformamide, N,N-dimethylacetamide, N-methylpyrrolidinone and the like can be used.

As the sulfoxide solvent, aprotic sulfoxides such as dimethyl sulfoxide and the like can be used.

As the sulfone solvent, aprotic sulfones such as ethyl methyl sulfone, ethyl isopropyl sulfone, 3-methylsulfolane, sulfolane and the like can be used.

As the hydrocarbon solvent, alicyclic hydrocarbons such as cyclohexane, methylcyclohexane and the like; and aromatic hydrocarbons such as benzene, toluene, xylene, mesitylene, ethylbenzene, tert-butylbenzene, trifluoromethylbenzene, nitrobenzene, chlorobenzene, chlorotoluene, bromobenzene and the like can be used.

As the basic organic solvent, pyridine solvents such as pyridine, 2-methylpyridine, 3-methylpyridine, 4-methylpyridine, 2,6-dimethylpyridine and the like can be used.

As the first organic solvent, hydrocarbon solvent is preferable. From the aspects of the operability, productivity, cost and the like, toluene, xylene and chlorobenzene are more preferable, and toluene is particularly preferable.

In addition, as the first organic solvent, a sulfone solvent is also preferable. From the aspects of reactivity, productivity and the like, sulfolane is preferable.

Furthermore, as the first organic solvent, a mixture of a hydrocarbon solvent and a sulfone solvent is also preferably used, and a mixture of toluene and sulfolane is particularly preferable. The mixing ratio (volume ratio) of the hydrocarbon solvent and the sulfone solvent can be appropriately selected within the range of 1:99-99:1.

The amount of the first organic solvent to be used is generally not less than 1 L, preferably not less than 2 L, further preferably not less than 3 L, per 1 kg of the carboxylic acid compound represented by the aforementioned formula (4), from the aspects of operability and the like, and the upper limit is generally not more than 50 L, preferably not more than 30 L, more preferably not more than 20 L, further preferably not more than 4.5 L, particularly preferably not more than 4 L, per 1 kg of the carboxylic acid compound represented by the aforementioned formula (4), from the aspects of the operability, productivity, cost and the like.

As the second organic solvent, a sulfone solvent is preferably used from the aspects of reactivity, productivity and the like. As the sulfone solvent, aprotic sulfone such as ethyl methyl sulfone, ethyl isopropyl sulfone, 3-methylsulfolane, sulfolane and the like can be used. It is particularly preferable to use sulfolane because the yield of the desired nitrile compound is improved. The sulfone solvent is preferably used alone, but may be used by mixing with other organic solvents (e.g., hydrocarbon solvent) in any ratio.

The amount of the second organic solvent to be used is generally not less than 1 L, preferably not less than 2 L, further preferably not less than 3 L, per 1 kg of the carboxylic acid compound represented by the aforementioned formula (4), from the aspects of operability and the like, and the upper limit is generally not more than 50 L, preferably not more than 30 L, more preferably not more than 20 L, further preferably not more than 4.5 L, particularly preferably not more than 4 L, per 1 kg of the carboxylic acid compound represented by the aforementioned formula (4), from the aspects of the operability, productivity, cost and the like.

The kind and amount of the catalyst to be used are the same as those in step 2B-1.

The reaction starting material 1 is prepared by mixing a carboxylic acid compound represented by the aforementioned formula (4), a halogenating agent, the first organic solvent and, where necessary, a catalyst. The preparation temperature is generally 15° C.-65° C., preferably 20° C.-60° C., particularly preferably 30° C.-50° C. When the preparation temperature is too low, the progress of the reaction may be delayed and the productivity may decrease, and when it is too high, many by-products may be produced and the quality of the desired nitrile compound may decrease.

The reaction starting material 1 may be subjected to concentration, purification and the like.

The reaction starting material 2 is prepared by mixing a compound represented by the aforementioned formula (7) and the second organic solvent. The preparation temperature is not particularly limited, and is generally 10° C.-180° C., preferably 20° C.-150° C.

The reaction starting materials 1 and 2 may contain, where necessary, inorganic additive (e.g., diatomaceous earth, silicic anhydride, silicon dioxide, sodium sulfate, magnesium sulfate, sodium chloride, magnesium chloride, calcium carbonate, magnesium carbonate, etc.). Using an inorganic additive, the reaction can proceed smoothly.

In this step, the reaction starting material 1 and the reaction starting material 2 may be mixed and the mixture may be heated and reacted at 80° C.-180° C., or the reaction starting material 1 at 80° C.-180° C. and the reaction starting material 2 at 80° C.-180° C. may be mixed and reacted. The reaction starting material 2 may be added to the reaction starting material 1 and mixed, or the reaction starting material 1 may be added to the reaction starting material 2 and mixed.

The time of reaction of the reaction starting material 1 and the reaction starting material 2 may vary depending on the halogenating agent, organic solvent, catalyst and the like to be used, and can be appropriately determined according to the progress of the reaction. It is generally 0.5 hr-30 hr, preferably 1 hr-15 hr, particularly preferably 2 hr-10 hr. The reaction is generally performed under normal pressure.

(3) Subsequent Step

The reaction mixture containing a nitrile compound represented by the formula (1), which is obtained in the aforementioned step 2A or 2B, may be subjected to a treatment such as neutralization, partitioning, filtration and the like, or the desired nitrile compound represented by the formula (1) may be isolated by an isolation means such as concentration, crystallization and the like.

The nitrile compound represented by the formula (1) obtained in the present invention has a high quality (HPLC) of preferably not less than 98%, particularly preferably not less than 99%. It may be further purified by a known purification means such as recrystallization, column chromatography and the like.

The production method of the present invention may be batch or continuous.

In addition, each compound in the present invention may form a solvate such as hydrate, organic solvent solvate, and the like, and the form thereof is not particularly limited as long as the reaction is not inhibited.

In the present invention, the following steps are particularly preferable.

step 1: a step of reacting 2'-acetonaphthone, sulfur and morpholine, followed by hydrolysis to give 2-naphthylacetic acid

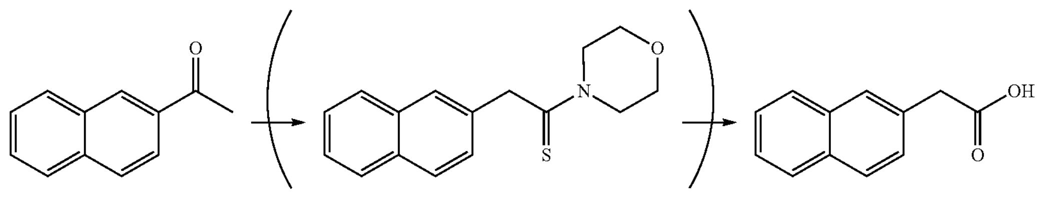

step 2A: a step of reacting 2-naphthylacetic acid, thionyl chloride, and ammonia (gas or aqueous solution) to give 2-naphthylacetamide, and further reacting the obtained compound with phosphoryl chloride to give 2-naphthylacetonitrile

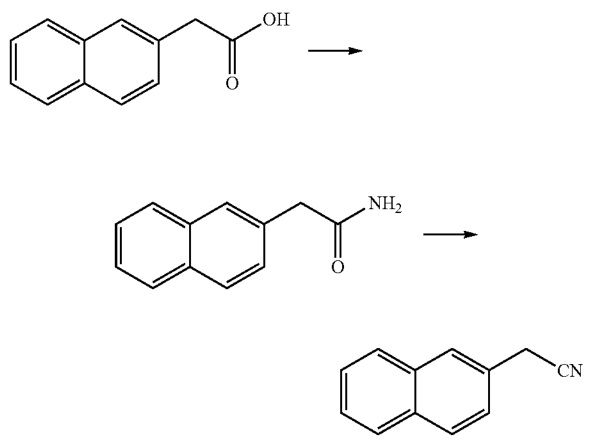

step 2B-1: a step of reacting 2-naphthylacetic acid, sulfolane, thionyl chloride, sulfamide and, where necessary, a catalyst at 80° C.-180° C. to give 2-naphthylacetonitrile

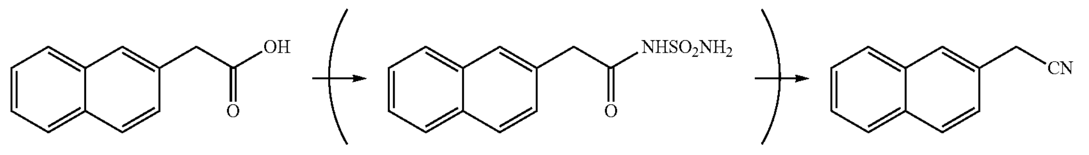

step 2B-2: a step of reacting reaction starting material 1 which is a mixture of 2-naphthylacetic acid, thionyl chloride, toluene and, where necessary, a catalyst with reaction starting material 2 which is a mixture of sulfamide and sulfolane at 80° C.-180° C. to give 2-naphthylacetonitrile

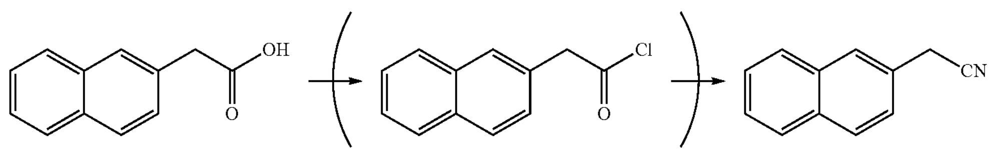

EXAMPLES

The present invention is described in more detail with reference to Examples; however, the present invention is not limited by these examples.

In the following Examples and Comparative Examples, commercially available 2'-acetonaphthone was used. The purity of the obtained compound was measured by HPLC under the following analysis conditions.

(HPLC Analysis Conditions-1)

- analysis instrument: HPLC (1200 series) manufactured by Agilent
- column: Cadenza CD-C18, 3 μm, 150 mm×4.6 mm
- mobile phase A: 0.1 volume % trifluoroacetic acid aqueous solution
- mobile phase B: acetonitrile
- gradient: 0 min (B: 15%)-15 min (B: 90%)-20 min (B: 90%)
- flow rate: 1.0 mL/min
- injection volume: 5 μL
- detection wavelength: 215 nm
- column temperature: 40° C.

(HPLC Analysis Conditions-2)

- analysis instrument: HPLC (1200 series) manufactured by Agilent
- column: Cadenza CD-C18, 3 μm, 150 mm×4.6 mm
- mobile phase A: 0.1 volume % trifluoroacetic acid aqueous solution
- mobile phase B: acetonitrile
- gradient: 0 min (B: 15%)-20 min (B: 90%)-25 min (B: 90%)
- flow rate: 1.0 mL/min
- injection volume: 5 μL
- detection wavelength: 280 nm
- column temperature: 40° C.

(HPLC Analysis Conditions-3)

- analysis instrument: HPLC (1200 series) manufactured by Agilent
- column: Zorbax Eclipse Plus Phenyl-Hexyl, 5 μm, 250 mm×4.6 mm
- mobile phase A: 0.1 volume % trifluoroacetic acid aqueous solution
- mobile phase B: acetonitrile
- gradient: 0 min (B: 30%)-15 min (B: 60%)-20 min (B: 95%)-30 min (B: 95%)
- flow rate: 1.0 mL/min
- injection volume: 5 μL
- detection wavelength: 280 nm
- column temperature: 40° C.

Example 1: Synthesis of Carboxylic Acid Compound

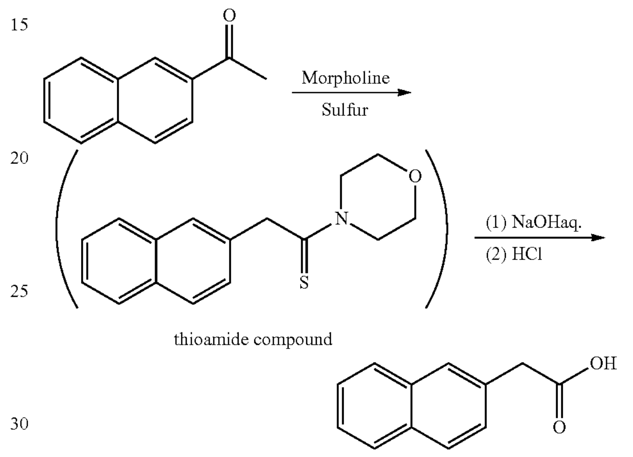

thioamide compound

In a nitrogen-substituted reactor were placed 2'-acetonaphthone (3.00 g) and sulfur (0.85 g, 1.5 mole ratio to 2'-acetonaphthone), morpholine (4.61 g, 3 mole ratio to 2'-acetonaphthone) was further added, and the mixture was reacted at 115° C.-125° C. for 4 hr (thioamide compound was produced).

The reaction mixture was cooled to 70° C.-80° C., sodium hydroxide aqueous solution at concentration 20 wt % (mixture of sodium hydroxide (3.53 g) and water (14.1 g), sodium hydroxide at 5 mole ratio to 2'-acetonaphthone) was added, and the mixture was reacted at 90° C.-105° C. for 8 hr (hydrolysis). The reaction mixture was cooled to 50° C.-60° C., activated carbon (Seisei Shirasagi, 0.15 g) was added, and the mixture was stirred and filtered. To the obtained filtrate was added hydrochloric acid at concentration 35% (mixture of hydrochloric acid (14.69 g) and water (12.4 mL)), and the mixture was stirred and cooled to recover 2-naphthylacetic acid as crude crystals.

The crude crystals (2.0 g) (purity (HPLC analysis conditions-1) 92.6%) of the obtained 2-naphthylacetic acid were dissolved in toluene (20 mL) at 115° C., and the mixture was cooled to not more than 10° C. to allow precipitation of a carboxylic acid compound. The obtained 2-naphthylacetic acid was 1.3 g, and the purity measured by HPLC (HPLC analysis conditions-1) was 98.2 Area %.

$^1$H-NMR (400 MHz, $CDCl_3$) δ 3.80 (2H, s), 7.40 (1H, dd, J=8.4, 3.0 Hz), 7.43-7.49 (2H, m), 7.73 (1H, s), 7.78-7.82 (3H, m)

Figure 2:
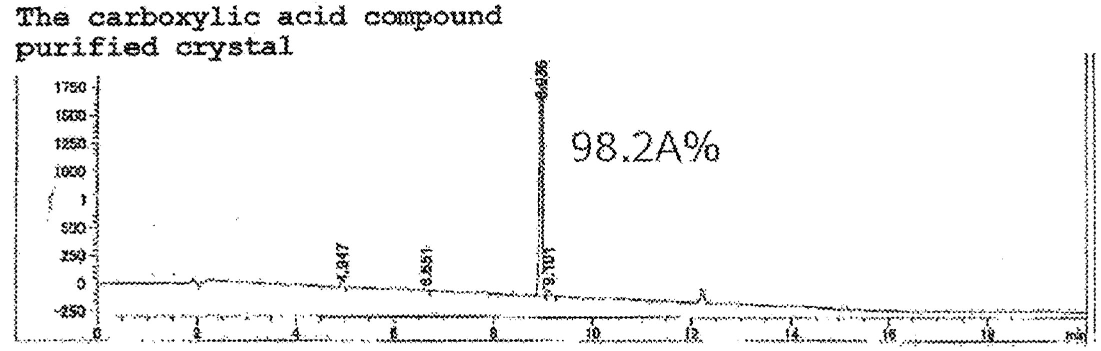
FIG. 2 shows the HPLC analysis results of purified crystals of the carboxylic acid compound obtained in Example 1.
Figure 3:
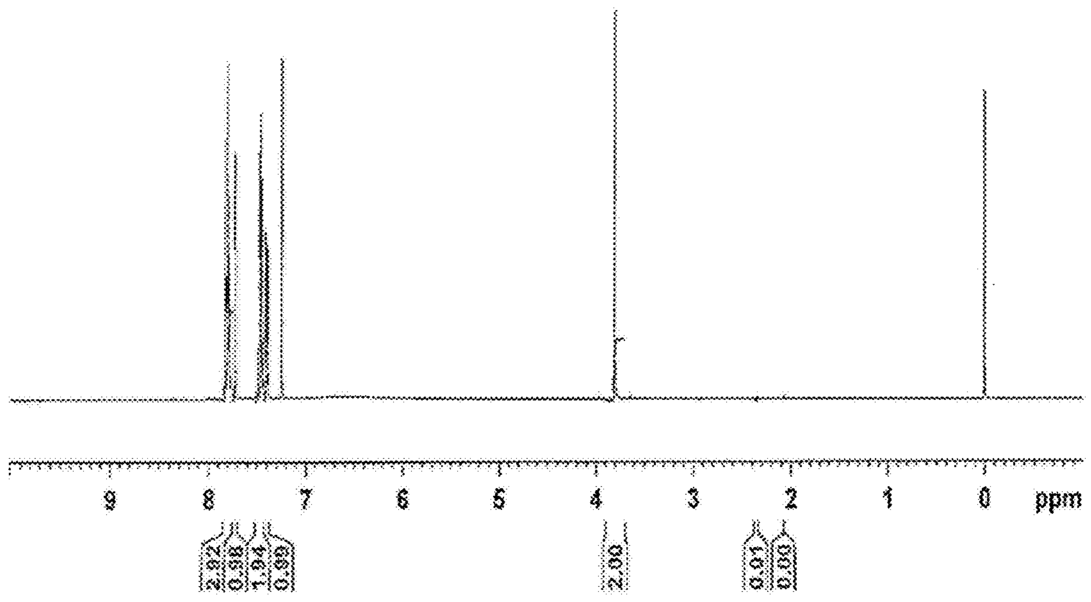
FIG. 3 shows the $^1$H-NMR measurement results of purified crystals of the carboxylic acid compound obtained in Example 1.

The HPLC analysis results of the crude crystals of the obtained carboxylic acid compound (2-naphthylacetic acid) are shown in FIG. 1. In addition, the HPLC analysis results of the purified crystals of the obtained carboxylic acid compound (2-naphthylacetic acid) are shown in FIG. 2, and the $^1$H-NMR measurement results are shown in FIG. 3.

Example 2: Synthesis of Carboxylic Acid Compound

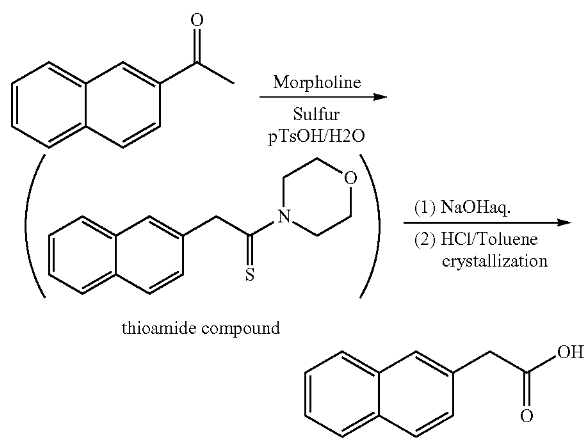

In a nitrogen-substituted reactor were placed 2'-acetonaphthone (120.00 g), sulfur (28.26 g, 1.25 mole ratio to 2'-acetonaphthone), p-toluenesulfonic acid monohydrate (13.41 g, 0.10 mole ratio to 2'-acetonaphthone) and morpholine (184.26 g, 3 mole ratio to 2'-acetonaphthone), and the mixture was stirred and reacted at 115° C.-125° C. for 9 hr (thioamide compound was produced).

The reaction mixture was cooled to 70° C.-80° C., sodium hydroxide aqueous solution at concentration 20 wt % (mixture of sodium hydroxide (141.00 g) and water (564.01 g), sodium hydroxide at 5 mole ratio to 2'-acetonaphthone) were added, and the mixture was reacted at 90° C.-105° C. for 4 hr (hydrolysis). The reaction mixture was cooled to 60° C.-70° C., water (120.00 g) and toluene (240.00 mL) were added, and the mixture was stirred at 65° C.-75° C. and left standing, after which the upper layer was discarded (removal of unreacted sulfur).

The obtained lower layer was added to a mixture of toluene (1200 mL) and hydrochloric acid at concentration 35% (mixture of hydrochloric acid (205.64 g) and water (281.90 mL), hydrochloric acid at 8 mole ratio to 2'-acetonaphthone). Furthermore, the reactor, wherein the lower layer had been contained, was washed by adding water (12.00 g), and the obtained liquid was also added to the mixture. The mixture of the aforementioned lower layer and the like was stirred at 65° C.-75° C., left standing (carboxylic acid compound extraction), and the obtained lower layer was discarded. Water (600.00 g) was added to the remaining upper layer, and the mixture was stirred at 65° C.-75° C. and left standing, and the lower layer was discarded. Water (600.00 g) was added to the remaining upper layer, and the mixture was stirred at 65° C.-75° C. and left standing, and the lower layer was discarded.

The obtained upper layer was concentrated, cooled to not more than 10° C., and the precipitated carboxylic acid compound (2-naphthylacetic acid) was recovered as crystals. The obtained carboxylic acid compound (2-naphthylacetic acid) was 104.14 g, and the purity measured by HPLC (HPLC analysis conditions-3) was 99.6 Area %.

$^1$H-NMR (400 MHz, $CDCl_3$) δ 3.80 (2H, s), 7.40 (1H, dd, J=8.4, 3.0 Hz), 7.43-7.49 (2H, m), 7.73 (1H, s), 7.78-7.82 (3H, m)

Figure 4:
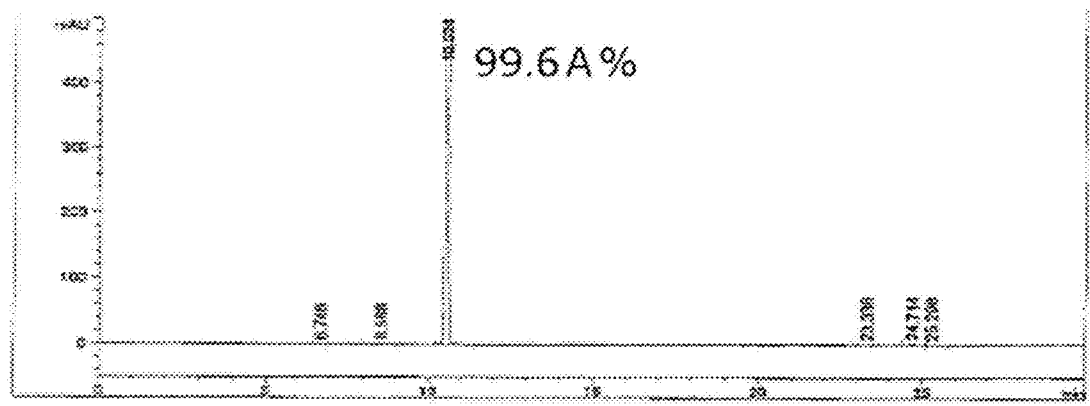
FIG. 4 shows the HPLC analysis results of the carboxylic acid compound obtained in Example 2.
Figure 5:
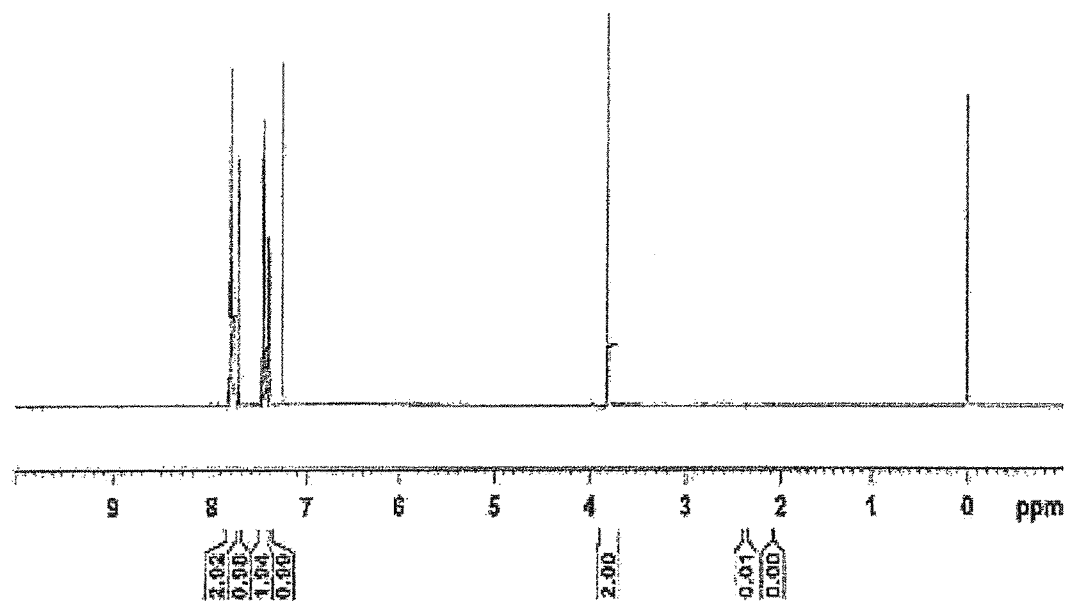
FIG. 5 shows the $^1$H-NMR measurement results of the carboxylic acid compound obtained in Example 2.

The HPLC analysis results of the obtained carboxylic acid compound (2-naphthylacetic acid) are shown in FIG. 4, and the $^1$H-NMR measurement results are shown in FIG. 5.

Example 3: Synthesis of Carboxylic Acid Compound

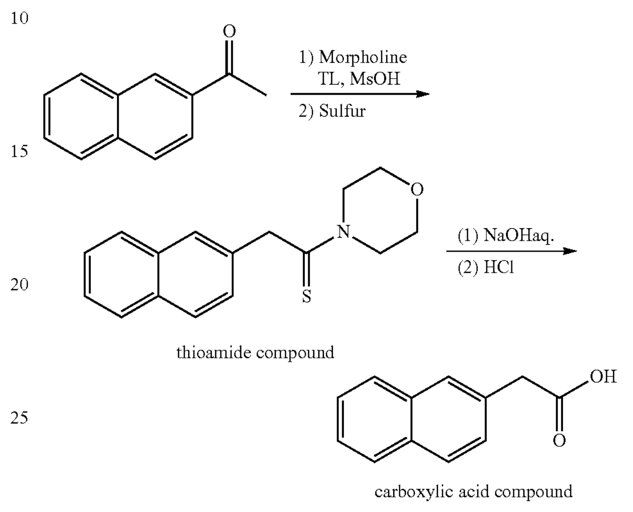

In a nitrogen-substituted reactor were placed 2'-acetonaphthone (120.00 g) and toluene (120 mL, 1.0 volume ratio to 2'-acetonaphthone), mesylic acid (0.34 g, 0.005 mole ratio to 2'-acetonaphthone), and morpholine (184.26 g, 3 mole ratio to 2'-acetonaphthone), and the mixture was stirred and distilled for 15 hr.

Thereafter, the mixture was concentrated, sulfur (28.26 g, 1.25 mole ratio to 2'-acetonaphthone) was added and the mixture was reacted at 95° C.-105° C. for 7 hr (thioamide compound was produced).

The reaction mixture was cooled to 70° C.-80° C., sodium hydroxide aqueous solution at concentration 20 wt % (mixture of sodium hydroxide (141.00 g) and water (564.01 g), sodium hydroxide at 5 mole ratio to 2'-acetonaphthone) was added, and the mixture was reacted at 90° C.-105° C. for 7 hr (hydrolysis). The reaction mixture was cooled to 60° C.-70° C., water (120.00 g) and toluene (240.00 mL) were added, and the mixture was stirred at 65° C.-75° C. and left standing, after which the upper layer was partitioned and discarded.

The obtained lower layer was added to a mixture of toluene (1200 mL) and hydrochloric acid at concentration 35% (mixture of hydrochloric acid (205.64 g) and water (281.90 mL), 8 mole ratio to 2'-acetonaphthone as hydrochloric acid). The mixture was stirred at 65° C.-75° C. and left standing, and the lower layer was discarded. Water (600.00 g) was added to the upper layer, and the mixture was stirred at 65° C.-75° C. and left standing, and the lower layer was discarded. Water (600.00 g) was added to the upper layer, and the mixture was stirred at 65° C.-75° C. and left standing, and the lower layer was discarded.

The obtained upper layer was concentrated, and cooled to not more than 10° C. to give 2-naphthylacetic acid as crystals. The obtained 2-naphthylacetic acid was 104.83 g, and the purity measured by HPLC (HPLC analysis conditions-3) was 99.8 Area %.

Comparative Example 1: Synthesis of Carboxylic Acid Compound

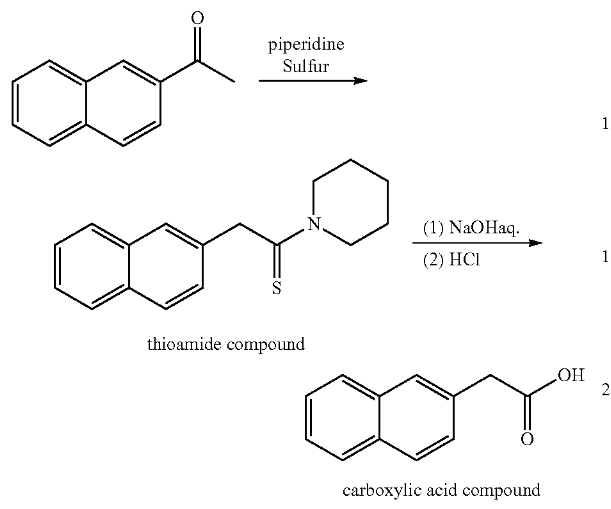

thioamide compound carboxylic acid compound

In a nitrogen-substituted reactor were added 2'-acetonaphthone (1.00 g) and sulfur (0.24 g, 1.25 mole ratio to 2'-acetonaphthone), and further piperidine (1.50 g, 3.0 mole ratio to 2'-acetonaphthone), and the mixture was stirred and then reacted at 115° C.-125° C. for 5 hr (thioamide compound was produced).

The reaction mixture was cooled to 70° C.-80° C., sodium hydroxide aqueous solution at concentration 20 wt % (mixture of sodium hydroxide (0.70 g) and water (2.82 g), sodium hydroxide at 3 mole ratio to 2'-acetonaphthone) was added, and the mixture was reacted at 90° C.-105° C. for 6 hr. Furthermore, sodium hydroxide aqueous solution at concentration 48 wt % (mixture of sodium hydroxide (0.70 g) and water (0.76 g), sodium hydroxide at 3 mole ratio to 2'-acetonaphthone) was added, and the mixture was reacted at 90° C.-105° C. for 3 hr (hydrolysis).

As a result of HPLC analysis (HPLC analysis conditions-3), a carboxylic acid compound (2-naphthylacetic acid) was produced at a purity of 7 Area %.

Since the yield of the carboxylic acid compound was small, it was considered that the reaction does not proceed sufficiently when piperidine is used instead of morpholine.

Reference Example 1: Synthesis of Thioamide Compound

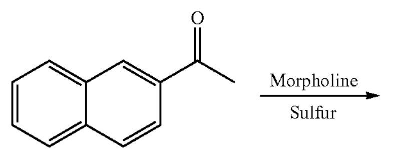

-continued

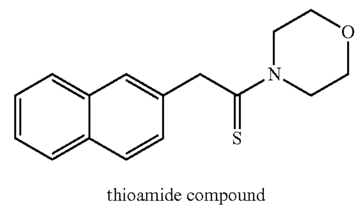

thioamide compound

In a nitrogen-substituted reactor were added 2'-acetonaphthone (1.00 g) and sulfur (0.20-0.28 g, 1.05-1.50 mole ratio to 2'-acetonaphthone), and morpholine (1.53 g, 3.0 mole ratio to 2'-acetonaphthone) was further added. The mixture was stirred and reacted at 80° C.-120° C. for 6-22 hr to synthesize a thioamide compound.

As a result of HPLC analysis (HPLC analysis conditions-3), a thioamide compound was produced at a purity of 77 Area %-85 Area %. The results are shown in Table 1.

Reference Example 2: Synthesis of Thioamide Compound

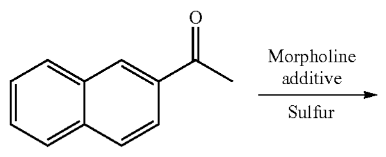

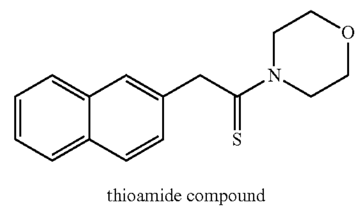

thioamide compound

In a nitrogen-substituted reactor were added 2'-acetonaphthone (1.00 g), sulfur (0.23 g, 1.25 mole ratio to 2'-acetonaphthone) and additive (see Table 1), and morpholine (1.54 g, 3.0 mole ratio to 2'-acetonaphthone) was further added. The mixture was stirred and reacted at 115° C.-125° C. for 3-25 hr to synthesize a thioamide compound.

As a result of HPLC analysis (HPLC analysis conditions-3), a thioamide compound was produced at a purity of 84 Area %-88 Area %. The results are shown in Table 1.

In Table 1, $Na_2SO_4$ is sodium sulfate, $MgSO_4$ is magnesium sulfate, pTsOH·$H_2O$ is p-toluenesulfonic acid monohydrate, and MsOH is methanesulfonic acid.

As is clear from Table 1, the production amount of the thioamide compound increases by using an appropriate additive.

TABLE 1

| | additive | amount of additive relative to 2'-acetonaphthone | amount of sulfur relative to 2'-acetonaphthone (mole ratio) | production amount of thioamide compound (Area %) | production amount of thiocarbamate compound (Area %) |
|---|---|---|---|---|---|
| Reference | — | — | 1.05 | 77.74 | 7.76 |
| Example 1 | — | — | 1.50 | 85.08 | 8.69 |
| | — | — | 1.25 | 83.73 | 8.32 |
| Reference | $Na_2SO_4$ | 3.0 mole ratio | 1.25 | 84.17 | 8.65 |
| Example 2 | $MgSO_4$ | 3.0 mole ratio | 1.25 | 86.44 | 7.48 |
| | Molecular Sieves 3A | 2.0 mass ratio | 1.25 | 88.11 | 4.93 |
| | $pTsOH•H_2O$ | 0.015 mole ratio | 1.25 | 84.21 | 7.49 |
| | $pTsOH•H_2O$ | 0.1 mole ratio | 1.25 | 86.95 | 6.04 |
| | $pTsOH•H_2O$ | 0.25 mole ratio | 1.25 | 84.34 | 7.84 |
| | MsOH | 0.25 mole ratio | 1.25 | 85.93 | 7.59 |
| | MsOH | 0.1 mole ratio | 1.25 | 84.49 | 7.56 |

Reference Example 3: Synthesis of Thioamide Compound

According to the method described in non-patent document 5 (Green Chemistry Letters and Reviews, 2010, 315-318), a thioamide compound was synthesized.

In a nitrogen-substituted reactor were placed 2'-acetonaphthone (1.00 g) and sulfur (0.21 g, 1.10 mole ratio to 2'-acetonaphthone), and morpholine (0.56 g, 1.10 mole ratio to 2'-acetonaphthone) and polyethylene glycol (PEG-600) (3.0 mL, 3.0 volume ratio to 2'-acetonaphthone) were further added. The mixture was stirred and reacted at 100° C. for 7 hr to synthesize a thioamide compound.

As a result of HPLC analysis (HPLC analysis conditions-3), a thioamide compound was produced at a purity of 34 Area %.

When polyethylene glycol was used, the yield of the thioamide compound was low, and improvement of reactivity by the use of polyethylene glycol could not be confirmed.

Example 4: Synthesis of Nitrile Compound

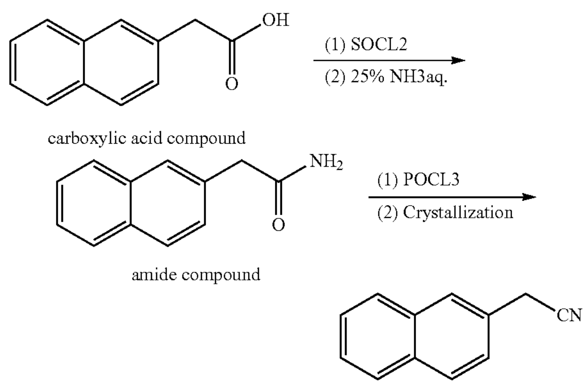

carboxylic acid compound amide compound

In a nitrogen-substituted reactor were mixed 2-naphthylacetic acid (0.50 g) obtained in Example 1, thionyl chloride (0.38 g, 1.2 mole ratio to carboxylic acid compound) and toluene (2.5 mL, 5.0 volume ratio to carboxylic acid compound), one drop of N,N-dimethylformamide was added as a catalyst, and the mixture was reacted at 40° C. for 3 hr (acid chlorination).

Furthermore, an acid chlorination reaction mixture was added dropwise to an aqueous ammonia solution at concentration 28% (0.82 g, ammonia at 5 mole ratio to carboxylic acid compound), and the mixture was reacted at 50° C. for 1 hr. The mixture was cooled to room temperature, and a precipitated amide compound was recovered by filtration (yield 77%).

The amide compound (0.40 g) obtained as mentioned above and phosphoryl chloride (0.36 g, 1.1 mole ratio to amide compound) were reacted at 85° C. for 4 hr. The obtained reaction mixture was subjected to a partitioning treatment, and the obtained organic layer was concentrated under reduced pressure. To the obtained concentration residue was added a mixture of 0.8 mL of toluene and 3.2 mL of heptane (2 and 8 volume ratio to amide compound, respectively). After stirring, precipitated 2-naphthylacetonitrile was recovered. The obtained 2-naphthylacetonitrile was 0.26 g, and the purity measured by HPLC (HPLC analysis conditions-2) was 97.2 Area %.

Figure 6:
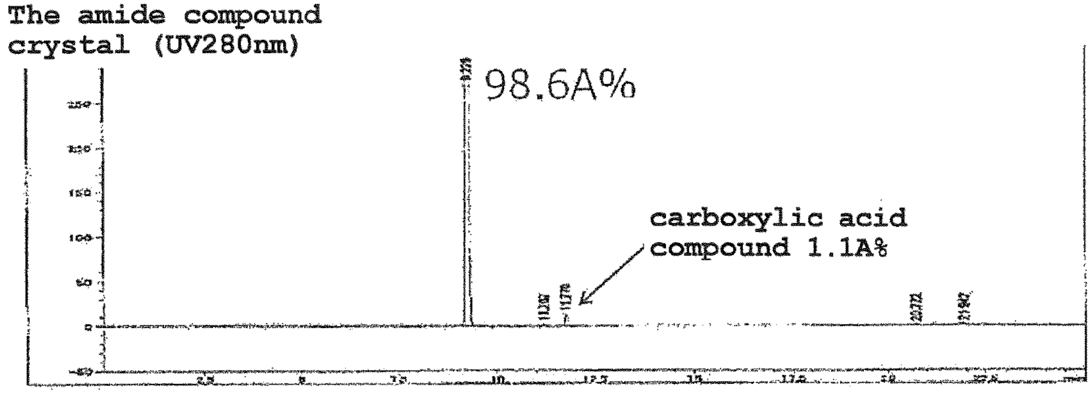
FIG. 6 shows the HPLC analysis results of the amide compound obtained in Example 4.
Figure 7:
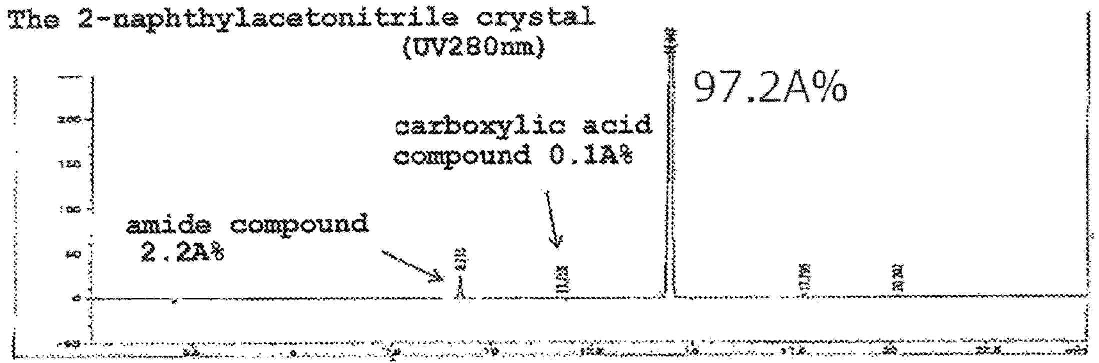
FIG. 7 shows the HPLC analysis results of the nitrile compound obtained in Example 4.

The HPLC analysis results (HPLC analysis conditions-2) of the obtained amide compound are shown in FIG. 6, and the HPLC analysis results of 2-naphthylacetonitrile are shown in FIG. 7.

Example 5: Synthesis of Nitrile Compound

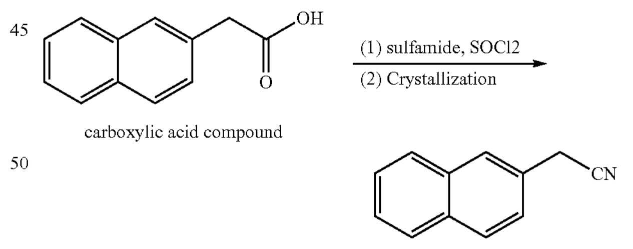

carboxylic acid compound

In a nitrogen-substituted reactor were placed 2-naphthylacetic acid (90.0 g) obtained in Example 2, sulfamide (51.1 g, 1.1 mole ratio to carboxylic acid compound), and sulfolane (315 mL, 3.5 volume ratio to carboxylic acid compound), and the mixture was stirred. The temperature was raised, and thionyl chloride (69.0 g, 1.2 mole ratio to carboxylic acid compound) was added at 95° C.-105° C. After reacting at 95° C.-105° C. for 7 hr, the reaction mixture was cooled, and activated carbon (Kyoryoku Shirasagi) (1.8 g, 0.02 weight ratio to carboxylic acid compound) and methanol (180 mL, 2 volume ratio to carboxylic acid compound) were added at 50° C.-60° C., and the mixture was stirred and filtered. The filtration residue was washed with methanol (90 mL, 1 volume ratio to carboxylic acid compound). The filtrate and the solution after washing were mixed, water (540 mL, 6 volume ratio to carboxylic acid compound) was added at 35° C.-45° C. The mixture was stirred, cooled to 0° C.-10° C., and precipitated 2-naphthylacetonitrile was recovered. The obtained 2-naphthylacetonitrile was 63.2 g, and the purity measured by HPLC (HPLC analysis conditions-3) was 99.5 Area %.

Figure 8:
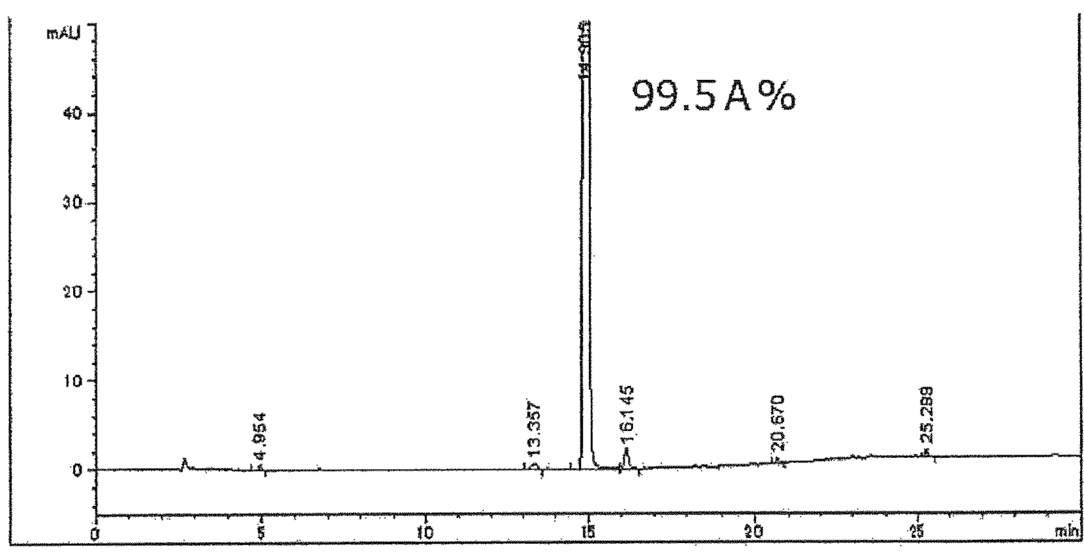
FIG. 8 shows the HPLC analysis results of the nitrile compound obtained in Example 5.
Figure 9:
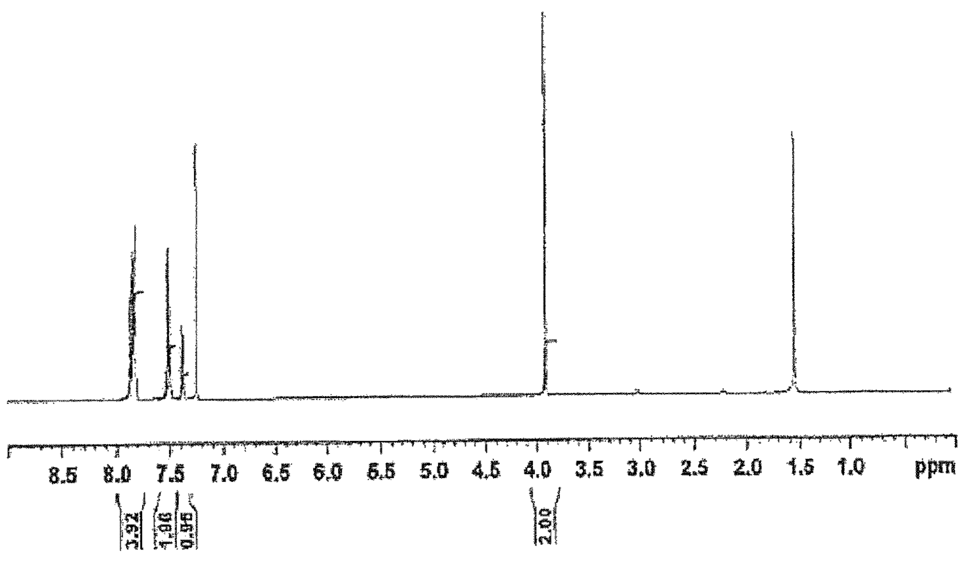
FIG. 9 shows the $^1$H-NMR measurement results of the nitrile compound obtained in Example 5.

The HPLC analysis results of the obtained 2-naphthylacetonitrile are shown in FIG. 8, and the $^1$H-NMR measurement results are shown in FIG. 9.

Example 6: Synthesis of Nitrile Compound

In a nitrogen-substituted reactor were mixed 2-naphthylacetic acid (1 g) synthesized in the same manner as in Example 2, toluene (10 mL, 10 volume ratio to 2-naphthylacetic acid), N,N-dimethylformamide (10 μL), and thionyl chloride (0.672 g, 1.05 mole ratio to 2-naphthylacetic acid), and the mixture was reacted at 40° C. for 3 hr, and the solvent was evaporated. The residue was mixed with sulfolane (10 mL, 10 volume ratio to 2-naphthylacetic acid) and sulfamide (0.620 g, 1.2 mole ratio to 2-naphthylacetic acid), and the mixture was reacted at 120° C. for 3 hr. The reaction product was analyzed by HPLC (HPLC analysis conditions-3). As a result, 2-naphthylacetonitrile was produced at a purity of 94.1 Area %.

Example 7: Synthesis of Nitrile Compound

In a nitrogen-substituted reactor were mixed 2-naphthylacetic acid (1.00 g) synthesized in the same manner as in Example 2, sulfolane (5 mL, 5 volume ratio to 2-naphthylacetic acid), and sulfamide (0.620 g, 1.2 mole ratio to 2-naphthylacetic acid), thionyl chloride (0.672 g, 1.05 mole ratio to 2-naphthylacetic acid) was added dropwise at 100° C., and the mixture was reacted by stirring at 100° C. for 8 hr. The reaction product was analyzed by HPLC (HPLC analysis conditions-3). As a result, 2-naphthylacetonitrile was produced at a purity of 96.8 Area %.

Comparative Example 2: Synthesis of Nitrile Compound

In a nitrogen-substituted reactor were mixed 2-naphthylacetic acid (1.00 g) synthesized in the same manner as in Example 2, toluene (10 mL, 10 volume ratio to 2-naphthylacetic acid), thionyl chloride (0.672 g, 1.05 mole ratio to 2-naphthylacetic acid), and N,N-dimethylformamide (10 μL), and the mixture was stirred at 40° C. for 1 hr. To the obtained reaction mixture was added sulfamide (0.620 g, 1.2 mole ratio to 2-naphthylacetic acid), and the mixture was reacted at 120° C. for 3 hr. The reaction product was analyzed by HPLC (HPLC analysis conditions-3). As a result, 2-naphthylacetonitrile was produced at a purity of 18.6 Area %.

Comparative Example 3: Synthesis of Nitrile Compound

In a nitrogen-substituted reactor were placed and mixed 2-naphthylacetic acid (1.00 g) synthesized in the same manner as in Example 2, toluene (10 mL, 10 volume ratio to 2-naphthylacetic acid), thionyl chloride (0.672 g, 1.05 mole ratio to 2-naphthylacetic acid), and N,N-dimethylformamide (10 μL), and the reaction mixture was stirred at 40° C. for 1 hr and then concentrated. Separately, the concentrated residue prepared earlier was added dropwise to a solution of sulfamide (0.620 g, 1.2 mole ratio to 2-naphthylacetic acid) and N-methylpyrrolidone (5 mL, 5 volume ratio to 2-naphthylacetic acid), and the mixture was reacted by stirring at 100° C. for 7 hr. The reaction product was analyzed by HPLC (HPLC analysis conditions-3). As a result, 2-naphthylacetonitrile was produced at a purity of 63.4 Area %.

Comparative Example 4: Synthesis of Nitrile Compound

In a nitrogen-substituted reactor were placed and mixed 2-naphthylacetic acid (1.00 g) synthesized in the same manner as in Example 2, sulfamide (0.620 g, 1.2 mole ratio to 2-naphthylacetic acid), N,N-dimethylformamide (10 μL), and acetonitrile (10 mL, 10 volume ratio to 2-naphthylacetic acid) and, under reflux, thionyl chloride (0.672 g, 1.05 mole ratio to 2-naphthylacetic acid) was added and the mixture was reacted for 1 hr. The reaction product was analyzed by HPLC (HPLC analysis conditions-3). As a result, 2-naphthylacetonitrile was produced at a purity of 0.3 Area %.

Comparative Example 5: Synthesis of Nitrile Compound

In a nitrogen-substituted reactor were placed and mixed 2-naphthylacetic acid (1 g) synthesized in the same manner as in Example 2, sulfolane (5 mL, 5 volume ratio to 2-naphthylacetic acid), and sulfamide (0.620 g, 1.2 mole ratio to 2-naphthylacetic acid), thionyl chloride (0.672 g, 1.05 mole ratio to 2-naphthylacetic acid) was added dropwise at 60° C., and the mixture was stirred at 60° C. for 2 hr. After stirring, since the reaction mixture was solidified due to the precipitated crystal components, the mixture was heated to 80° C. and stirred. By stirring at 80° C., a solution state was achieved, and the mixture was reacted by stirring in that state for 5 hr. The reaction product was analyzed by HPLC (HPLC analysis conditions-3). As a result, 2-naphthylacetonitrile was not detected.

Example 8: Synthesis of Nitrile Compound

In a nitrogen-substituted reactor were added 2-naphthylacetic acid amide (0.4 g) synthesized in the same manner as in Example 4, toluene (2.8 mL, 7 volume ratio to 2-naphthylacetic acid amide), and phosphorus oxychloride (0.364 g, 1.1 mole ratio to 2-naphthylacetic acid amide), and the mixture was reacted by stirring at 80° C. for 2 hr. The reaction product was analyzed by HPLC (HPLC analysis conditions-3). As a result, 2-naphthylacetonitrile was produced at a purity of 95.2 Area %.

Example 9: Synthesis of Nitrile Compound

In a nitrogen-substituted reactor were added 2-naphthylacetic acid amide (0.3 g) synthesized in the same manner as in Example 4, toluene (4 mL, 13.3 volume ratio to 2-naphthylacetic acid amide), and cyanuric chloride (0.328 g, 1.1 mole ratio to 2-naphthylacetic acid amide), and the mixture was reacted by stirring at 120° C. for 6 hr. The reaction product was analyzed by HPLC (HPLC analysis conditions-3). As a result, 2-naphthylacetonitrile was produced at a purity of 73.8 Area %.

Example 10: Synthesis of Nitrile Compound

In a nitrogen-substituted reactor were added 2-naphthylacetic acid amide (0.3 g) synthesized in the same manner as in Example 4, toluene (4.0 mL, 13.3 volume ratio to 2-naphthylacetic acid amide), and phosphorus pentoxide (0.253 g, 1.1 mole ratio to 2-naphthylacetic acid amide), and the mixture was reacted by stirring at 80° C. for 5 hr. The reaction product was analyzed by HPLC (HPLC analysis conditions-3). As a result, 2-naphthylacetonitrile was produced at a purity of 94.1 Area %.

Example 11: Synthesis of Nitrile Compound

In a nitrogen-substituted reactor were added an amide compound (2-naphthylacetic acid amide) (0.3 g) synthesized in the same manner as in Example 4, toluene (4.0 mL, 13.3 volume ratio to 2-naphthylacetic acid amide), p-toluenesulfonyl chloride (0.341 g, 1.1 mole ratio to 2-naphthylacetic acid amide), and pyridine (0.327 μL, 2.5 mole ratio to 2-naphthylacetic acid amide), and the mixture was reacted by stirring at 120° C. for 1.5 hr. The reaction product was analyzed by HPLC (HPLC analysis conditions-3). As a result, 2-naphthylacetonitrile was produced at a purity of 84.8 Area %.

Comparative Example 6: Synthesis of Nitrile Compound

In a nitrogen-substituted reactor were added an amide compound (2-naphthylacetic acid amide) (0.3 g) synthesized in the same manner as in Example 4, toluene (3 mL, 10 volume ratio to 2-naphthylacetic acid amide), and thionyl chloride (0.251 g, 1.3 mole ratio to 2-naphthylacetic acid amide), and the mixture was reacted by stirring at 90° C. for 15 hr. The reaction product was analyzed by HPLC (HPLC analysis conditions-3). As a result, 2-naphthylacetonitrile was produced at a purity of 34.4 Area %.

Comparative Example 7: Synthesis of Nitrile Compound

In a nitrogen-substituted reactor were added an amide compound (2-naphthylacetic acid amide) (0.3 g) synthesized in the same manner as in Example 4, toluene (4.0 mL, 13.3 volume ratio to 2-naphthylacetic acid amide), p-toluenesulfonyl chloride (0.341 g, 1.1 mole ratio to 2-naphthylacetic acid amide), and trimethylamine (0.563 μL, 2.5 mole ratio to 2-naphthylacetic acid amide), and the mixture was reacted by stirring at 120° C. for 9.5 hr. The reaction product was analyzed by HPLC (HPLC analysis conditions-3). As a result, 2-naphthylacetonitrile was produced at a purity of 51.6 Area %.

Comparative Example 8: Synthesis of Nitrile Compound

In a nitrogen-substituted reactor were added an amide compound (2-naphthylacetic acid amide) (0.3 g) synthesized in the same manner as in Example 4, toluene (3.0 mL, 10.0 volume ratio to 2-naphthylacetic acid amide), trimethylamine (0.409 g, 2.5 mole ratio to 2-naphthylacetic acid amide), dimethyl sulfoxide (1.2 μL, 0.01 mole ratio to 2-naphthylacetic acid amide), and oxalyl chloride (0.247 g, 1.2 mole ratio to 2-naphthylacetic acid amide), and the mixture was reacted by stirring at 25° C. for 1 hr. The reaction product was analyzed by HPLC (HPLC analysis conditions-3). As a result, 2-naphthylacetonitrile was produced at a purity of 28.2 Area %.

Example 12: Synthesis of 2-Naphthylacetonitrile

In a nitrogen-substituted reactor were placed and mixed 2-naphthylacetic acid (1.00 g) obtained in the same manner as in Example 2, sulfolane (3.5 mL, 3.5 volume ratio to 2-naphthylacetic acid), and sulfamide (0.620 g, 1.2 mole ratio to 2-naphthylacetic acid), thionyl chloride (0.704 g, 1.1 mole ratio to 2-naphthylacetic acid) was added dropwise at 100° C., and the mixture was reacted by stirring at 100° C. for 7.5 hr. The reaction product was analyzed by HPLC (HPLC analysis conditions-3). As a result, 2-naphthylacetonitrile was produced at a purity of 96.2 Area %.

Comparative Example 9: Synthesis of 2-Naphthylacetonitrile

In a nitrogen-substituted reactor were placed and mixed 2-naphthylacetic acid (1.00 g) obtained in the same manner as in Example 2, sulfolane (3.5 mL, 3.5 volume ratio to 2-naphthylacetic acid), and sulfamide (0.568 g, 1.1 mole ratio to 2-naphthylacetic acid), thionyl chloride (0.768 g, 1.2 mole ratio to 2-naphthylacetic acid) was added dropwise at 100° C., and the mixture was reacted by stirring at 100° C. for 4.5 hr. The reaction product was analyzed by HPLC (HPLC analysis conditions-3). As a result, 2-naphthylacetonitrile was produced at a purity of 84.1 Area %.

Comparative Example 10: Synthesis of 2-Naphthylacetonitrile

In a nitrogen-substituted reactor were placed and mixed a carboxylic acid compound (2-naphthylacetic acid) (0.5 g) obtained in the same manner as in Example 2, sulfolane (1.5 mL, 3 volume ratio to 2-naphthylacetic acid), and sulfamide (0.284 g, 1.1 mole ratio to 2-naphthylacetic acid), and thionyl chloride (0215 μL, 1.1 mole ratio to 2-naphthylacetic acid) was added dropwise at 100° C. Sulfolane (0.25 mL, 0.5 volume ratio to 2-naphthylacetic acid) was further added, and the mixture was reacted by stirring at 100° C. for 7.5 hr. The reaction product was analyzed by HPLC (HPLC analysis conditions-3). As a result, 2-naphthylacetonitrile was produced at a purity of 79.2 Area %.

TABLE 2

| | amount of sulfamide relative to 2-naphthylacetic acid (mole ratio) | amount of thionyl chloride relative to 2-naphthylacetic acid (mole ratio) | reaction time (hr) | purity of 2-naphthylacetonitrile (Area %) | amount of high polar impurities at RT = 2-4 min (Area %) |
|---|---|---|---|---|---|
| Example 12 | 1.2 | 1.1 | 7.5 | 96.2 | 1.0 |
| Comparative Example 9 | 1.1 | 1.2 | 4.5 | 84.1 | 7.8 |
| Comparative Example 10 | 1.1 | 1.1 | 7.5 | 79.2 | 1.7 |

As is clear from Table 2, high purity 2-naphthylacetonitrile can be obtained when the amount of sulfamide is greater than the amount of thionyl chloride (Example 12). On the other hand, when the amount of sulfamide is smaller than the amount of thionyl chloride, many high polar impurities are produced as by-products, and the obtained 2-naphthylacetonitrile has low purity (Comparative Example 9). When the amount of sulfamide is the same as the amount of thionyl chloride, the amount of high polar impurities produced as by-products is relatively small, and it is considered that the reaction did not proceed sufficiently due to the low purity of 2-naphthylacetonitrile.

Comparative Example 11: Bromination Method

A method for synthesizing 2-(bromomethyl)naphthalene from 2-methylnaphthalene was studied.

(1) Synthesis of 2-(bromomethyl)naphthalene

In a nitrogen-substituted reactor were added commercially available 2-methylnaphthalene (1.0 g), cyclohexane (4.0 mL, 4.0 volume ratio to 2-methylnaphthalene), N-bromosuccinimide (NBS) (1.00 g-1.46 g, 0.80-1.17 mole ratio to 2-methylnaphthalene) and azobisisobutyronitrile (AIBN) (3.5 mg, 0.003 mole ratio to 2-methylnaphthalene), and the mixture was reacted at 40° C., 60° C., and 80° C. (reflux) for 2 hr. After the reaction, the mixture was cooled to room temperature, and the reaction was discontinued by adding 20 wt % sodium hydroxide aqueous solution (2.0 mL). Thereafter, the upper layer was analyzed by HPLC (HPLC analysis conditions-1) and the reaction composition was analyzed. The results are shown in Table 3.

In the following Table 3-Table 5, MR is a mole ratio to 2-methylnaphthalene, VR is a volume ratio to 2-methylnaphthalene, c-Hex is cyclohexane, Product is 2-(bromomethyl)naphthalene, S.M. is 2-methylnaphthalene, DiBr is a dibromo form, A % is Area % by HPLC analysis, and N.D. means not detected.

TABLE 3

| Run | | 1 | 2 | 3 | 4 | 5 |
|---|---|---|---|---|---|---|
| Bromination Reagent (MR) | | NBS 1.17 | NBS 1.17 | NBS 0.80 | NBS 1.00 | NBS 1.17 |
| AIBN (MR) | | 0.003 | 0.003 | 0.003 | 0.003 | 0.003 |
| Solvent (VR) | | c-Hex/4.0 | c-Hex/4.0 | c-Hex/4.0 | c-Hex/4.0 | c-Hex/4.0 |
| Reaction Temp. (° C.) | | 40 | 60 | reflux | reflux | reflux |
| Aging | Product (A %) | N.D. | N.D. | 54.00 | 67.88 | 71.83 |
| 2.0 | S.M. (A %) | 100 | 100 | 40.94 | 23.27 | 12.21 |
| hr | DiBr (A %) | N.D. | N.D. | 2.53 | 5.49 | 11.82 |

(2) Synthesis of 2-(bromomethyl)naphthalene

In a nitrogen-substituted reactor were added commercially available 2-methylnaphthalene (1.0 g), cyclohexane (4.0 mL, 4.0 volume ratio to 2-methylnaphthalene), 1,3-dibromo-5,5-dimethylhydantoin (DBMH) (0.91-1.21 g, 0.45-0.60 mole ratio to 2-methylnaphthalene), and azobisisobutyronitrile (AIBN) (3.5 mg, 0.003 mole ratio to 2-methylnaphthalene), and the mixture was reacted at 80° C. (reflux) for 2 hr. After the reaction, the mixture was cooled to room temperature, and the reaction was discontinued by adding 20 wt % sodium hydroxide aqueous solution (2.0 mL). Thereafter, the upper layer was analyzed by HPLC (HPLC analysis conditions-1) and the reaction composition was analyzed. The results are shown in Table 4.

TABLE 4

| Run | | 6 | 7 |
|---|---|---|---|
| Bromination Reagent (MR) | | DBMH 0.6 | DBMH 0.45 |
| AIBN (MR) | | 0.003 | 0.003 |
| Solvent (VR) | | c-Hex/4.0 | c-Hex/4.0 |
| Reaction Temp. (° C.) | | reflux | reflux |
| Aging | Product (A %) | 69.28 | 59.51 |
| 2.0 hr | S.M. (A %) | 21.14 | 34.54 |
| | DiBr (A %) | 5.70 | 3.24 |

(3) Synthesis of 2-(bromomethyl)naphthalene

In a nitrogen-substituted reactor were added commercially available 2-methylnaphthalene (1.0 g), a solvent (4.0 mL, 4.0 volume ratio to 2-methylnaphthalene), 1,3-dibromo-5,5-dimethylhydantoin (DBMH) (1.21 g, 0.60 mole ratio to 2-methylnaphthalene), and azobisisobutyronitrile (AIBN) (3.5 mg, 0.003 mole ratio to 2-methylnaphthalene), and the mixture was reacted at 80° C. for 2 hr. After the reaction, the mixture was cooled to room temperature, and the reaction was discontinued by adding 20 wt % sodium hydroxide aqueous solution (2.0 mL). Thereafter, the upper layer was analyzed by HPLC (HPLC analysis conditions-1) and the reaction composition was analyzed. The results are shown in Table 5.

TABLE 5

| Run | | 6 | 8 | 9 | 10 |
|---|---|---|---|---|---|
| Bromination Reagent (MR) | | DBMH 0.6 | DBMH 0.6 | DBMH 0.6 | DBMH 0.6 |
| AIBN (MR) | | 0.003 | 0.003 | 0.003 | 0.003 |
| Solvent (VR) | | c-Hex 4.0 | ClPh 4.0 | CF3Ph 4.0 | o-DiCLPh 4.0 |
| Reaction Temp. (° C.) | | reflux | 80 | 80 | 80 |
| Aging | Product (A %) | 69.28 | 31.33 | 25.86 | 26.90 |
| 2.0 hr | S.M. (A %) | 21.14 | 9.80 | 13.82 | 6.38 |
| | DiBr (A %) | 5.70 | 1.14 | 0.64 | 0.77 |

※ ClPh: Chlorobenzene, CF3Ph: Trifluorotoluene, oDiCLPh: 1, 2-dichlorobenzene

From the above examination results, it could be confirmed that when the yield of the desired product (2-(bromomethyl) naphthalene) is increased, a by-product dibromo form increases, and it is necessary to lower the yield of the desired product to suppress the production of the dibromo form. Subsequent studies also revealed that it is difficult to improve this relationship, and it is difficult to improve the yield in the synthesis of 2-(bromomethyl)naphthalene by bromination of 2-methylnaphthalene.

(4) Synthesis of 2-naphthylacetonitrile from 2-(bromomethyl)naphthalene 2-(bromomethyl)naphthalene (2.0 g, containing 17 Area % of dibromo form) synthesized by a method similar to that in the above-mentioned Run6, dimethyl sulfoxide (10.0 mL, 5.0 volume ratio to 2-(bromomethyl)naphthalene), and sodium cyanide (0.89 g, 2.0 mole ratio to 2-(bromomethyl) naphthalene) were added, and the mixture was reacted at 40° C. for 3.5 hr. After the reaction, water (10.0 mL, 5.0 volume ratio to 2-(bromomethyl)naphthalene) was added dropwise and crystals were precipitated. After cooling, the mixture was stirred at 13° C. for 2.5 hr, and the crystals were recovered by filtration. The obtained crystals were analyzed by HPLC (HPLC analysis conditions-1). As a result, 2-naphthylacetonitrile was produced at a purity of 60.2 Area % and the dibromo form was contained at 5.4 Area %.

INDUSTRIAL APPLICABILITY

The present invention can provide a novel method for industrially producing highly pure aromatic nitrile compounds such as 2-naphthylacetonitrile and the like and highly pure aromatic carboxylic acid compounds such as 2-naphthylacetic acid and the like, that are useful as starting materials for synthesis, or intermediates for synthesis of various pharmaceutical products, agricultural chemicals, and chemical products, safely and highly efficiently at low costs. Furthermore, using the thus-obtained aromatic nitrile compounds such as 2-naphthylacetonitrile and the like, pharmaceutical products such as (1R,5S)-1-(naphthalen-2-yl)-3-azabicyclo[3.1.0]hexane and the like can be produced safely at low costs.

The invention claimed is:

1. A method for producing a carboxylic acid compound represented by the formula (4')

(4')

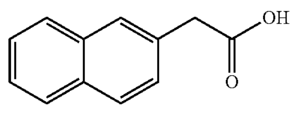

comprising subjecting a compound represented by the formula (2')

(2')

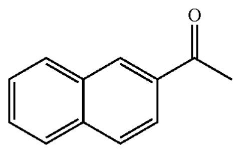

to Willgerodt reaction in the presence of molecular sieves, magnesium sulfate, p-toluenesulfonic acid, or methanesulfonic acid, thereby suppressing the production of a ketothioamide compound represented by the following formula

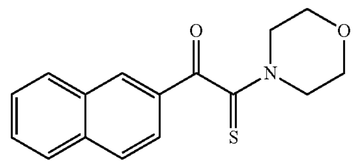 [SMILES: O=C(C(=S)N1CCOCC1)c1ccc2ccccc2c1]

to give a compound represented by the formula (3')

(3')

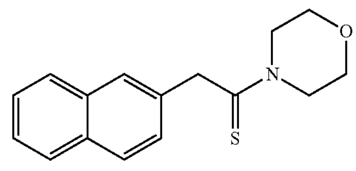

and hydrolyzing and thereafter neutralizing the obtained compound represented by the formula (3') to give a carboxylic acid compound represented by the aforementioned formula (4').

2. The method for producing a carboxylic acid compound according to claim 1, wherein, after the aforementioned hydrolysis, the reaction product obtained by the hydrolysis is contacted with toluene; toluene is present during the aforementioned neutralization; or the reaction product obtained by the aforementioned neutralization is contacted with toluene.

3. The method for producing a carboxylic acid compound according to claim 1, wherein the compound of the aforementioned formula (4') has a sulfur content of 0.001 mol % to 1 mol %, and a purity of not less than 98 mol %.

4. A carboxylic acid compound represented by the formula (4')

(4')

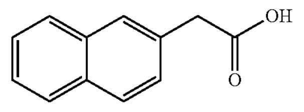

wherein said compound has a sulfur content of 0.001 mol % to 1 mol %, and a purity of not less than 98 mol %.

5. A method for producing a nitrile compound represented by the formula (1')

(1')

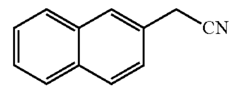

comprising the following step 1 and step 2A:

step 1:

subjecting a compound represented by the formula (2')

(2')

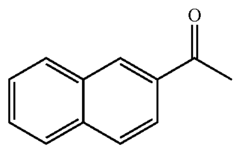

to Willgerodt reaction in the presence of an additive as necessary to give an amide compound represented by the formula (3')

(3')

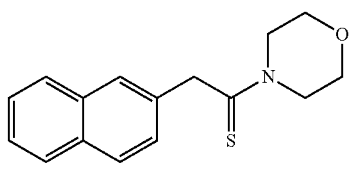

and hydrolyzing with a base and thereafter neutralizing the obtained compound to give a carboxylic acid compound represented by the formula (4')

(4')

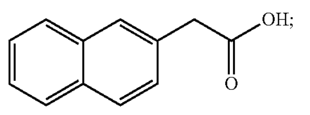

step 2A:

reacting the carboxylic acid compound represented by the aforementioned formula (4'), obtained in the aforementioned step 1, with a halogenating agent in the presence of a catalyst as necessary in an organic solvent, further reacting the obtained compound with an amidating agent to give a compound represented by the formula (5')

(5')

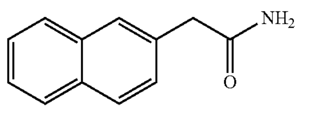

or the formula (6')

(6')

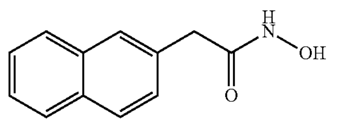

and reacting the obtained compound with a dehydrating agent to give a nitrile compound represented by the aforementioned formula (1').

6. The method for producing a nitrile compound according to claim 5, wherein the base is an alkali metal hydroxide, an alkaline earth metal hydroxide, an alkali metal carbonate, an alkaline earth metal carbonate, an alkali metal hydrogen carbonate, an alkaline earth metal hydrogen carbonate, or an alkali metal alkoxide.

7. The method for producing a nitrile compound according to claim 5, wherein the amount of the base is 1 mol to 10 mol per 1 mol of the amide compound represented by the aforementioned formula (3').

8. The method for producing a nitrile compound according to claim 5, wherein a temperature of the hydrolysis is 80° C. to 115° C.

9. The method for producing a nitrile compound according to claim 5, wherein, in the aforementioned step 1, the amide compound represented by the aforementioned formula (3') is obtained by subjecting the compound represented by the aforementioned formula (2') to the Willgerodt reaction in the presence of molecular sieves, magnesium sulfate, p-toluenesulfonic acid, or methanesulfonic acid as the additive, thereby suppressing the production of a ketothioamide compound represented by the following formula

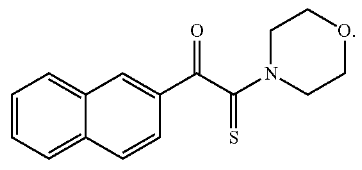 [SMILES: O=C(C(=S)N1CCOCC1)c1ccc2ccccc2c1]

10. The method for producing a nitrile compound according to claim 5, wherein, in the aforementioned step 1, the Willgerodt reaction is conducted by reacting the compound represented by the aforementioned formula (2') with sulfur and morpholine at a temperature from 90° C. to 150° C.

11. The method for producing a nitrile compound according to claim 10, wherein the amount of the sulfur is 1 mol to 3 mol per 1 mol of the compound represented by the aforementioned formula (2'), and the amount of the morpholine is 2 mol to 6 mol per 1 mol of the compound represented by the aforementioned formula (2').

12. The method for producing a nitrile compound according to claim 5, wherein, in the aforementioned step 2A, the carboxylic acid compound represented by the aforementioned formula (4') is reacted with the halogenating agent in the presence of N,N-dimethylformamide, N-methylpyrrolidone, or N,N-dimethylacetamide as the catalyst in the organic solvent at a temperature from 20° C. to 60° C.

13. The method for producing a nitrile compound according to claim 5, wherein, in the aforementioned step 2A, the halogenating agent is thionyl chloride, oxalyl chloride, sulfuryl chloride, phosphoryl chloride, phosphorus trichloride, phosphorus pentachloride, thionyl bromide, or phosphorus tribromide.

14. The method for producing a nitrile compound according to claim 5, wherein, in the aforementioned step 2A, the amidating agent is ammonia or hydroxyamine.

15. The method for producing a nitrile compound according to claim 5, wherein, in the aforementioned step 2A, the dehydrating agent is phosphorus pentoxide, polyphosphoric acid, phosphorus pentachloride, thionyl chloride, phosphoryl chloride, acetyl chloride, tosyl chloride/pyridine, cyanuric chloride, benzenesulfonyl chloride, oxalyl chloride, or phosphorus tribromide.

16. The method for producing a carboxylic acid compound according to claim 1, wherein the compound represented by the formula (3') is hydrolyzed with a base.

17. The method for producing a carboxylic acid compound according to claim 16, wherein the base is an alkali metal hydroxide, an alkaline earth metal hydroxide, an alkali metal carbonate, an alkaline earth metal carbonate, an alkali metal hydrogen carbonate, an alkaline earth metal hydrogen carbonate, or an alkali metal alkoxide.

18. The method for producing a carboxylic acid compound according to claim 16, wherein the amount of the base is 1 mol to 10 mol per 1 mol of the compound represented by the aforementioned formula (3').

19. The method for producing a carboxylic acid compound according to claim 16, wherein a temperature of the hydrolysis is 80° C. to 115° C.

20. The method for producing a carboxylic acid compound according to claim 16, wherein the Willgerodt reaction is conducted by reacting the compound represented by the aforementioned formula (2') with sulfur and morpholine at a temperature from 90° C. to 150° C.

21. The method for producing a carboxylic acid compound according to claim 20, wherein the amount of the sulfur is 1 mol to 3 mol per 1 mol of the compound represented by the aforementioned formula (2'), and the amount of the morpholine is 2 mol to 6 mol per 1 mol of the compound represented by the aforementioned formula (2').

* * * * *